United States Patent
Akahoshi et al.

(10) Patent No.: US 7,504,423 B2
(45) Date of Patent: Mar. 17, 2009

(54) α-AMINO ACID DERIVATIVES AND USE THEREOF AS MEDICINES

(75) Inventors: Fumihiko Akahoshi, Tokyo (JP); Yoshiharu Hayashi, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 188 days.

(21) Appl. No.: 10/582,602

(22) PCT Filed: Dec. 10, 2004

(86) PCT No.: PCT/JP2004/018479

§ 371 (c)(1), (2), (4) Date: Jun. 30, 2006

(87) PCT Pub. No.: WO2005/056541

PCT Pub. Date: Jun. 23, 2005

(65) Prior Publication Data

US 2007/0049619 A1  Mar. 1, 2007

(30) Foreign Application Priority Data

Dec. 11, 2003  (JP)  ............... 2003-413846

(51) Int. Cl.
  A01N 43/78  (2006.01)
  A61K 31/425  (2006.01)
  C07D 277/04  (2006.01)
  C07D 277/08  (2006.01)

(52) U.S. Cl. .................... 514/365; 548/146

(58) Field of Classification Search .............. None
See application file for complete search history.

(56) References Cited

U.S. PATENT DOCUMENTS

| | | |
|---|---|---|
| 6,548,481 B1 | 4/2003 | Demuth et al. |
| 6,849,622 B2 | 2/2005 | Yasuda et al. |
| 7,026,316 B2 | 4/2006 | Ashton et al. |
| 2003/0134802 A1 | 7/2003 | Demuth et al. |
| 2004/0063935 A1 | 4/2004 | Yasuda et al. |
| 2004/0106656 A1 | 6/2004 | Ashton et al. |
| 2004/0229926 A1 | 11/2004 | Yasuda et al. |
| 2005/0054678 A1 | 3/2005 | Yasuda et al. |
| 2005/0203030 A1 | 9/2005 | Demuth et al. |

FOREIGN PATENT DOCUMENTS

| | | |
|---|---|---|
| JP | 2004-244412 A | 9/2004 |
| WO | WO 99/61431 A1 | 12/1999 |
| WO | WO 02/30891 A1 | 4/2002 |
| WO | WO 02/076450 A1 | 10/2002 |

OTHER PUBLICATIONS

STN registry, structure with RN 855341-78-5, entered into STN Jul. 15, 2005.*
Heymann et al., *FEBS Letters*, 91(2): 360-364 (Jul. 1978).
Schön et al., *Biomed. Biochim. Acta*, 44(2): K9-K15 (1985).
Johnson et al., *The Journal of Cell Biology*, 121(6): 1423-1432 (1993).
Callebaut et al., *Science*, 262: 2045-2050 (Dec. 24, 1993).
Deacon et al., *Journal of Clinical Endocrinology and Metabolism*, 80(3): 952-957 (1995).
Deacon et al., *American Journal of Physiology*, 271: E458-E464 (1996).
Knudsen et al., *European Journal of Pharmacology*, 318: 429-435 (1996).
Wiedeman et al., *Current Opinion in Investigation Drugs*, 4(4): 412-420 (2003).
Caldwell et al., *Bioorganic & Medicinal Chemistry Letters*, 14: 1265-1268 (2004).
Parmee et al., *Bioorganic & Medicinal Chemistry Letters*, 14: 43-46 (2004).

* cited by examiner

*Primary Examiner*—James O Wilson
*Assistant Examiner*—Noble Jarrell
(74) *Attorney, Agent, or Firm*—Leydig, Voit & Mayer, Ltd.

(57) ABSTRACT

Compounds represented by the α-amino acid derivative or a pharmaceutically acceptable salt thereof of the present invention have a therapeutic effect due to a DPP-IV inhibitory action and useful as pharmaceutical agents for the treatment and/or prophylaxis of diseases relating to a DPP-IV inhibitor.

10 Claims, No Drawings

α-AMINO ACID DERIVATIVES AND USE THEREOF AS MEDICINES

TECHNICAL FIELD

The present invention relates to an α-amino acid derivative having a DPP-IV inhibitory action, use thereof as medicines and production method thereof.

BACKGROUND ART

DPP-IV is a serine protease, which recognizes an amino acid sequence having proline (or alanine or hydroxyproline) the penultimate position from the N-terminal and produces dipeptide Xaa-Pro (Xaa shows an optional amino acid and Pro shows L-proline). DPP-IV is widely distributed in mammalian tissues and is known to be present particularly in blood, kidney, intestinal epithelium and placenta.

While the physiological role of DPP-IV in mammal has not been completely elucidated, its involvement in a broad range of functions of living organisms such as degradation of neuropeptide (see non-patent reference 1), activation of T cell (see non-patent reference 2), adhesion of metastatic tumor cell to endothelium (see non-patent reference 3), invasion of HIV virus into lymphocytes (see non-patent reference 4) and the like is being clarified. Of these, the role of DPP-IV as an enzyme that inactivates glucagon-like peptide (GLP-1), which is a biogenic substance having a strong insulin secretion ability and controls postprandial blood glucose level, has been drawing attention (see non-patent reference 5).

GLP-1 is known to be metabolized in several minutes in a living organism. In the metabolism, that by DPP-IV is particularly important, because DPP-IV quickly cleaves GLP-1 to produce inert GLP-1 (see non-patent reference 6). In addition, it is considered that physiological action of GLP-1 becomes attenuated further because this inert GLP-1 shows an antagonistic action on GLP-1 receptor (see non-patent reference 7). Therefore, a method for suppressing cleavage of GLP-1 by inhibition of DPP-IV is considered to be the most superior approach for reinforcing GLP-1 action. That is, a DPP-IV inhibitor is expected to be a superior treatment method of curing postprandial hyperglycemia without side effects, such as prolonged hypoglycemia and the like, for non insulin-dependent diabetic (type II diabetes) patients.

Patent applications directed to DPP-IV inhibitors have been already filed.

A compound consisting of a natural amino acid and thiazolidine or pyrrolidine is known to show a DPP-IV inhibitory action (see patent reference 1). Besides this reference, compounds consisting of cyclohexylglycines and thiazolidine have been disclosed (see patent reference 2).

patent reference 1: WO99/61431
patent reference 2: WO02/76450
non-patent reference 1: Heymann et al., FEBS Letters, vol. 91, 360-364 (1978).
non-patent reference 2: Schon et al., Biomedica Biochimica Acta., vol. 44, K9-K15 (1985).
non-patent reference 3: Johnson et al., Journal of Cell Biology, vol. 121, 1423-1432 (1993).
non-patent reference 4: Callebaut et al., Science, vol. 262, 2045-2050 (1993).
non-patent reference 5: Deacon et al., Journal of Clinical Endocrinology and Metabolism, vol. 80, 952-957 (1995).
non-patent reference 6: Deacon et al., American Journal of Physiology, vol. 271, E458-E464 (1996).
non-patent reference 7: Knudsen et al., European Journal of Pharmacology, vol. 318, 429-435 (1996).

DISCLOSURE OF THE INVENTION

Problems to be Solved by the Invention

There are many reports on DPP-IV inhibitors to the present [Wiedeman et al., Current Opinion in Investigational Drugs, vol. 4, 412-420 (2003) etc.]. While they influenced the progress of drug discovery techniques, a compound providing sufficient clinical effects has not been reported, and the development of a more effective inhibitor has been desired.

Means of Solving the Problems

In view of the above-mentioned points, the present inventors have conducted intensive studies with the aim of developing a novel DPP-IV inhibitor. As a result, the present inventors have found that α-amino acid derivatives have potent DPP-IV inhibitory activities, and made the stability higher, which resulted in the completion of the present invention.

Accordingly, the subject matter of the present invention rests in the following (1) to (12).

(1) An α-amino acid derivative of the formula (I)

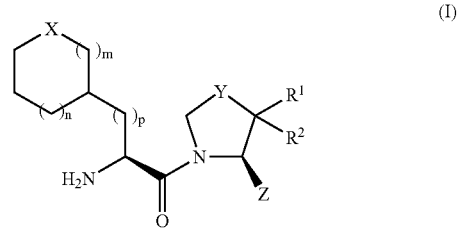

wherein
$R^1$ is a hydrogen atom, a halogen atom, alkyl or alkoxy,
$R^2$ is a hydrogen atom, a halogen atom, a hydroxyl group, alkyl or alkoxy, or
$R^1$ and $R^2$ are joined to form oxo, hydroxyimino, alkoxyimino or alkylidene,
X is CH—$R^3$ or N—$R^4$,
Y is $CR^5R^6$
 wherein $R^5$ and $R^6$ are each a hydrogen atom, a halogen atom, a hydroxyl group, alkyl or alkoxy, or
 $R^5$ and $R^6$ are optionally joined to form oxo, hydroxyimino, alkoxyimino or alkylidene,
 S, S=O or $SO_2$,
Z is a hydrogen atom or cyano,
m and n are each 0, 1 or 2, wherein the sum of m and n is 1, 2 or 3,
p is 0, 1, 2 or 3,
$R^3$ is —$NR^7R^8$
 wherein $R^7$ and $R^8$ are optionally the same or different and each independently is a hydrogen atom, alkyl, cycloalkyl, cycloalkylalkyl, aryl, arylalkyl, heteroaryl or heteroarylalkyl, or are optionally bonded to each other to form heterocycle having at least one nitrogen atom, and optionally having other further hetero atom(s),
 wherein the heterocycle is optionally substituted or condensed with an aromatic ring optionally having substituent(s),
—$NR^9COR^{10}$
wherein $R^9$ and $R^{10}$ are optionally the same or different and each independently is a hydrogen atom, alkyl, cycloalkyl, cycloalkylalkyl, aryl, arylalkyl, arylalkenyl, heteroaryl, heteroarylalkyl or heterocycle,
—$NR^{11}CONR^{12}R^{13}$ wherein $R^{11}$, $R^{12}$ and $R^{13}$ are optionally the same or different and each independently is a hydrogen atom, alkyl, cycloalkyl, cycloalkylalkyl, aryl, arylalkyl, heteroaryl or heteroarylalkyl, or $R^{12}$ and $R^{13}$ are optionally bonded to each other to form heterocycle having at least one nitrogen atom, and optionally having other further hetero atom(s), wherein the heterocycle is optionally substituted or condensed with an aromatic ring optionally having substituent(s),

—$NR^{14}SO_2R^{15}$ wherein $R^{14}$ and $R^{15}$ are optionally the same or different and each independently is a hydrogen atom, alkyl, cycloalkyl, cycloalkylalkyl, aryl, arylalkyl, heteroaryl, heteroarylalkyl or heterocycle, —$OR^{16}$ or —$OCOR^{17}$ wherein $R^{16}$ and $R^{17}$ are each a hydrogen atom, alkyl, cycloalkyl, cycloalkylalkyl, aryl, arylalkyl, heteroaryl, heteroarylalkyl or heterocycle, and $R^4$ is a hydrogen atom, alkyl, cycloalkyl, cycloalkylalkyl, aryl, arylalkyl, heteroaryl, heteroarylalkyl, heterocycle, —$COR^{18}$ wherein $R^{18}$ is a hydrogen atom, alkyl, cycloalkyl, cycloalkylalkyl, aryl, arylalkyl, arylalkenyl, heteroaryl, heteroarylalkyl or heterocycle,

—$CONR^{19}R^{20}$ wherein $R^{19}$ and $R^{20}$ are optionally the same or different and each independently is a hydrogen atom, alkyl, cycloalkyl, cycloalkylalkyl, aryl, arylalkyl, heteroaryl or heteroarylalkyl, or $R^{19}$ and $R^{20}$ are optionally bonded to each other to form heterocycle having at least one nitrogen atom, and optionally having other further hetero atom(s), wherein the heterocycle is optionally substituted or condensed with an aromatic ring optionally having substituent(s), or

—$SO_2R^{21}$ wherein $R^{21}$ is alkyl, cycloalkyl, cycloalkylalkyl, aryl, arylalkyl, heteroaryl, heteroarylalkyl or heterocycle, provided that when p is 0, then X is CH—$R^3$, and $R^3$ shows the formula (II)

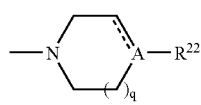

wherein

----- is a single bond or a double bond, $R^{22}$ is aryl or heteroaryl,

Q is 1 or 2, and

A is a carbon atom or a nitrogen atom, provided that i) when A is a carbon atom, then A is optionally substituted by a hydroxyl group, carboxyl or alkoxycarbonyl, and ii) when A is a nitrogen atom, then ----- is a single bond, wherein, of the above-mentioned groups, alkyl, cycloalkyl, cycloalkylalkyl, aryl, arylalkyl, heteroaryl, heteroarylalkyl and heterocycle optionally have substituent(s), or a pharmaceutically acceptable salt thereof.

(2) The α-amino acid derivative of the aforementioned (1), wherein, in the formula (I) of the aforementioned (1), m=2, n=0 and X=CH—$R^3$, or a pharmaceutically acceptable salt thereof.

(3) The α-amino acid derivative of the aforementioned (2), wherein, in the formula (I) of the aforementioned (1), $R^3$ is the formula (II) of the aforementioned (1), or a pharmaceutically acceptable salt thereof.

(4) The α-amino acid derivative of the aforementioned (3), wherein, in the formula (I) of the aforementioned (1), Y=S and $R^1$=$R^2$=Z=H, and in the formula (II) of the aforementioned (1), q=1 and A=N, or a pharmaceutically acceptable salt thereof.

(5) A compound of the formula (III)

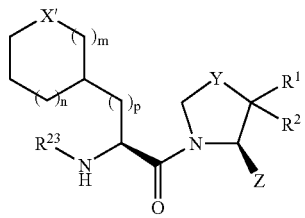

wherein

X" is CH—$R^3$, N—$R^4$ or C=O, $R^{23}$ is —$COR^{24}$ wherein $R^{24}$ is a hydrogen atom, alkyl, cycloalkyl, cycloalkylalkyl, aryl, arylalkyl, heteroaryl, heteroarylalkyl or heterocycle, or

—$COOR^{25}$ wherein $R^{25}$ is alkyl, cycloalkyl, cycloalkylalkyl, aryl, arylalkyl, heteroaryl, heteroarylalkyl or heterocycle, and other symbols are as defined in the aforementioned (1).

(6) The compound of the aforementioned (5), wherein, in the formula (III), X'=C=O.

The present invention also relates to the following pharmaceutical composition, inhibitor, and therapeutic agent.

(7) A pharmaceutical composition comprising an α-amino acid derivative of any of the aforementioned (1) to (4) or a pharmaceutically acceptable salt thereof and a pharmacologically acceptable carrier.

(8) A DPP-IV inhibitor comprising an α-amino acid derivative of any of the aforementioned (1) to (4) or a pharmaceutically acceptable salt thereof.

(9) An agent for the prophylaxis and/or treatment of a disease relating to a DPP-IV inhibitor, which comprises an α-amino acid derivative of any of the aforementioned (1) to (4) or a pharmaceutically acceptable salt thereof as an active ingredient.

(10) An agent for the prophylaxis and/or treatment of diabetes or obesity, which comprises an α-amino acid derivative of any of the aforementioned (1) to (4) or a pharmaceutically acceptable salt thereof as an active ingredient.

(11) The method of producing a compound of the aforementioned (5) wherein X' is represented by CH—$R^3$, which comprises use of a compound of the aforementioned (6) as an intermediate.

(12) The method of producing a compound of any of the aforementioned (1) to (4), which comprises the production method of the aforementioned (11).

Effect of the Invention

The compound of the present invention shows a potent DPP-IV inhibitory activity and is useful for the prophylaxis and/or treatment of diabetes or the prophylaxis and/or treatment of obesity.

BEST MODE FOR EMBODYING THE INVENTION

The present invention is explained in detail in the following.

Alkyl is, for example, linear or branched chain alkyl having 1 to 10 carbon atoms such as methyl, ethyl, propyl, isopropyl, butyl, isobutyl, sec-butyl, tert-butyl, pentyl, isopentyl, neopentyl, hexyl, heptyl, octyl, nonyl, decyl and the like, with preference given to lower alkyl having 1 to 6 carbon atoms and the like.

Cycloalkyl is, for example, cycloalkyl having 3 to 7 carbon atoms such as cyclopropyl, cyclobutyl, cyclopentyl, cyclohexyl, cycloheptyl and the like, and the like. The cycloalkyl may be condensed with a benzene ring to form indane (e.g., indan-1-yl, indan-2-yl etc.), tetrahydronaphthalene (e.g., tetrahydronaphthalen-5-yl, tetrahydronaphthalen-6-yl etc.) and the like (preferably indane etc.), and the cycloalkyl may be crosslinked via a linear atom chain having 1 or 2 carbon atoms to form a crosslinked cyclic hydrocarbon residue such as bicyclo[2.2.1]heptyl, bicyclo[2.2.2]octyl, bicyclo[3.2.2]nonyl and the like (preferably, cyclohexyl having crosslink via a linear atom chain having 1 or 2 carbon atoms etc., more preferably, bicyclo[2.2.1]heptyl etc.).

Cycloalkylalkyl comprises a cycloalkyl moiety as defined above, and an alkyl moiety, which is preferably a linear or branched chain having 1 to 3 carbon atoms, and is exemplified by cyclopropylmethyl, 2-cyclobutylethyl, 3-cyclopentylpropyl, cyclohexylmethyl, 2-cyclohexylethyl, cycloheptylmethyl and the like.

Aryl is preferably aryl having 6 to 14 carbon atoms and, for example, phenyl, naphthyl, an ortho fused bicyclic group having 8 to 10 ring atoms, wherein at least one ring is an aromatic ring (e.g., indenyl etc.) and the like can be mentioned.

Arylalkyl comprises an aryl moiety as mentioned above and an alkyl moiety which may be preferably a linear or branched chain having 1 to 3 carbon atoms and, for example, benzyl, benzhydryl, phenethyl, 3-phenylpropyl, 1-naphthylmethyl, 2-(1-naphthyl)ethyl, 2-(2-naphthyl)ethyl, 3-(2-naphthyl)propyl and the like can be mentioned.

Heteroaryl is preferably a 5- or 6-membered ring group having carbon and 1 to 4 hetero atoms (oxygen, sulfur or nitrogen), or ortho fused bicyclic heteroaryl having 8 to 10 ring atoms induced therefrom, particularly, a benz derivative, a derivative obtained by fusing with a propenylene, trimethylene or tetramethylene group, stable N-oxide thereof and the like. For example, pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl(2-pyridyl, 3-pyridyl, 4-pyridyl), pyrazinyl, pyrimidinyl, pyridazinyl, 1,2,4-triazinyl, 1,2,3-triazinyl, 1,3,5-triazinyl, benzoxazolyl, benzisoxazolyl, benzothiazolyl, benzisothiazolyl, benzimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indolinyl, indazolyl, isoquinolyl, quinolyl, phthalazinyl, quinoxalinyl, quinazolinyl, cinnolinyl, 2,1,3-benzoxadiazolyl, benzoxazinyl and the like can be mentioned.

Heteroarylalkyl comprises a heteroaryl moiety as defined above and the like, and an alkyl moiety which may be preferably a linear or branched chain having 1 to 3 carbon atoms, and, for example, 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl, 4-imidazolylmethyl and the like can be mentioned.

Heterocycle is saturated or unsaturated and has at least one nitrogen atom, and optionally has other further hetero atom(s) (oxygen or sulfur). It includes not only monocycles but also a spiro ring, with preference given to a 10- or 11-membered ring group, which is a spiro ring, or a 4- or 7-membered monocyclic ring group. As the heterocycle, for example, azetidinyl, pyrrolidinyl, piperidino, piperazinyl, morpholino, 1,4-diazepanyl, 1,2,5,6-tetrahydropyridyl, thiomorpholino, oxothiomorpholino, dioxothiomorpholino, 3-azaspiro[5.5]undecyl, 1,3,8-triazaspiro[4.5]decyl and the like can be mentioned.

The above-mentioned heterocycle may be substituted or condensed with an aromatic ring optionally having substituent(s). As the aromatic ring of the aromatic ring optionally having substituent(s), for example, benzene ring, pyridine ring and the like can be mentioned. As the fused ring, for example, indolinyl, isoindolinyl, 1,2,3,4-tetrahydroquinolyl, 1,2,3,4-tetrahydroisoquinolyl, phthalimido, indolyl, benz-3-azepine and the like can be mentioned.

Alkoxy is, for example, linear or branched chain alkoxy having 1 to 10 carbon atoms, such as methoxy, ethoxy, propoxy, isopropoxy, butoxy, pentyloxy, hexyloxy, octyloxy and the like, with preference given to lower alkoxy having 1 to 6 carbon atoms and the like.

As halogen, chlorine, bromine, fluorine and iodine can be mentioned.

As haloalkyl, trifluoromethyl, 2,2,2-trifluoroethyl, pentafluoroethyl and the like can be mentioned.

Of the above-mentioned substituent(s), alkyl, cycloalkyl, cycloalkylalkyl, aryl, arylalkyl, heteroaryl, heteroarylalkyl and heterocycle are each optionally substituted by one or more substituents shown below.

As these substituents, for example, halogen, hydroxyl group, nitro, cyano, trifluoromethyl, alkyl, alkoxy, alkylthio, cycloalkyl, cycloalkylalkyl, aryl, arylalkyl, heteroaryl, heteroarylalkyl, heterocycle, formyl, acyloxy, oxo, $-COOR_a$, $-CH_2COOR_a$, $-OCH_2COOR_a$, $-CONR_bR_c$, $-CH_2CQNR_bR_c$ (Q is =O or =S), $-OCH_2CONR_bR_c$, $-COO(CH_2)_2NR_eR_f$, $-SO_2T_1$, $-CONR_dSO_2T_1$, $-NR_eR_f$, $-NR_gCHO$, $-NR_gCOT_2$, $-NR_gCOOT_2$, $NR_gCONR_iR_j$, $-NR_kSO_2T_3$, $-SO_2NR_1R_m$, $-SO_2NR_nOCT_4$, methylenedioxy, ethyleneoxy and the like can be mentioned.

These substituents may further have substituent(s) and, for example, as aryl having substituent(s), heteroaryl having substituent(s) and heterocycle having substituent(s), 4-cyanophenyl, 4-chlorophenyl, 4-methoxyphenyl, 4-hydroxyphenyl, 4-fluorophenyl, 2,4-dichlorophenyl, 2-chloro-4-methoxyphenyl, 2,4-difluorophenyl, 5-cyano-2-pyridyl, 5-chloro-2-pyridyl, 1-ethoxycarbonyl-4-piperidinyl and the like can be mentioned.

Here, as the substituent(s) of the above-mentioned substituents, halogen, alkyl, alkoxy, cycloalkyl, cycloalkylalkyl, aryl, arylalkyl, heteroaryl, heteroarylalkyl and heterocycle are as defined above.

Alkylthio is, for example, linear or branched chain alkylthio having 1 to 10 carbon atoms such as methylthio, ethylthio, propylthio, butylthio, pentylthio, hexylthio, octylthio and the like, with preference given to lower alkylthio having 1 to 6 carbon atoms and the like.

Acyloxy is, for example, linear or branched chain acyloxy having 1 to 10 carbon atoms such as formyloxy, acetyloxy, propionyloxy, butyryloxy, valeryloxy, pivaloyloxy, hexanoyloxy, benzoyloxy and the like, with preference given to lower acyloxy having 1 to 6 carbon atoms and the like.

$R_a$ to $R_n$ are each hydrogen, alkyl (as defined above) or arylalkyl (as defined above).

$R_b$ and $R_c$, $R_e$ and $R_f$, $R_i$ and $R_j$, and $R_l$ and $R_m$ of —$NR_bR_c$, —$NR_eR_f$, —$NR_iR_j$ and —$NR_lR_m$ are each optionally bonded to each other to form heterocycle having at least one nitrogen atom, and optionally having other further hetero atom(s), wherein the heterocycle is optionally substituted or condensed with an aromatic ring optionally having substituent(s) (as defined above, optionally substituted by the aforementioned substituent(s)).

Moreover, —$NR_eR_f$ may show heteroaryl having =O (e.g., 2-pyrrolidinon-1-yl, succinimido, oxazolidin-2-on-3-yl, 2-benzoxazolinon-3-yl, phthalimido, cis-hexahydrophthalimido etc.).

$T_1$ to $T_4$ are each a hydrogen atom, alkyl, cycloalkyl, cycloalkylalkyl, aryl, arylalkyl, heteroaryl, heteroarylalkyl or haloalkyl, which is optionally substituted by the aforementioned substituent(s). Q is =O or =S.

The disease relating to a DPP-IV inhibitor is a disease for which a DPP-IV inhibitor is expected to show a prophylaxis and/or treatment effect, such as a disease developed by a DPP-IV action, a disease whose symptom is aggravated by a DPP-IV action, a disease whose cure is delayed by a DPP-IV action and the like. Specific preferable examples include diabetes, obesity and the like.

The compound (I) can show polymorphism, and can be present as two or more tautomers.

Therefore, the present invention encompasses any of the above-mentioned stereoisomers, optical isomers, polymorphs, tautomers, optional mixtures thereof and the like.

The pharmaceutically acceptable salt of compound (I) includes, inorganic acid addition salts (e.g., salts with hydrochloric acid, hydrobromic acid, hydriodic acid, sulfuric acid, phosphoric acid and the like), organic acid addition salts (e.g., salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like), salts with amino acids (e.g., salts with glutamic acid, aspartic acid and the like), and the like.

The α-amino acid derivative of the present invention can be produced by the following method.

Scheme 1 shows a production method of a compound (I) wherein m=2, n=0 and X=CH—OH or CH—$NH_2$.

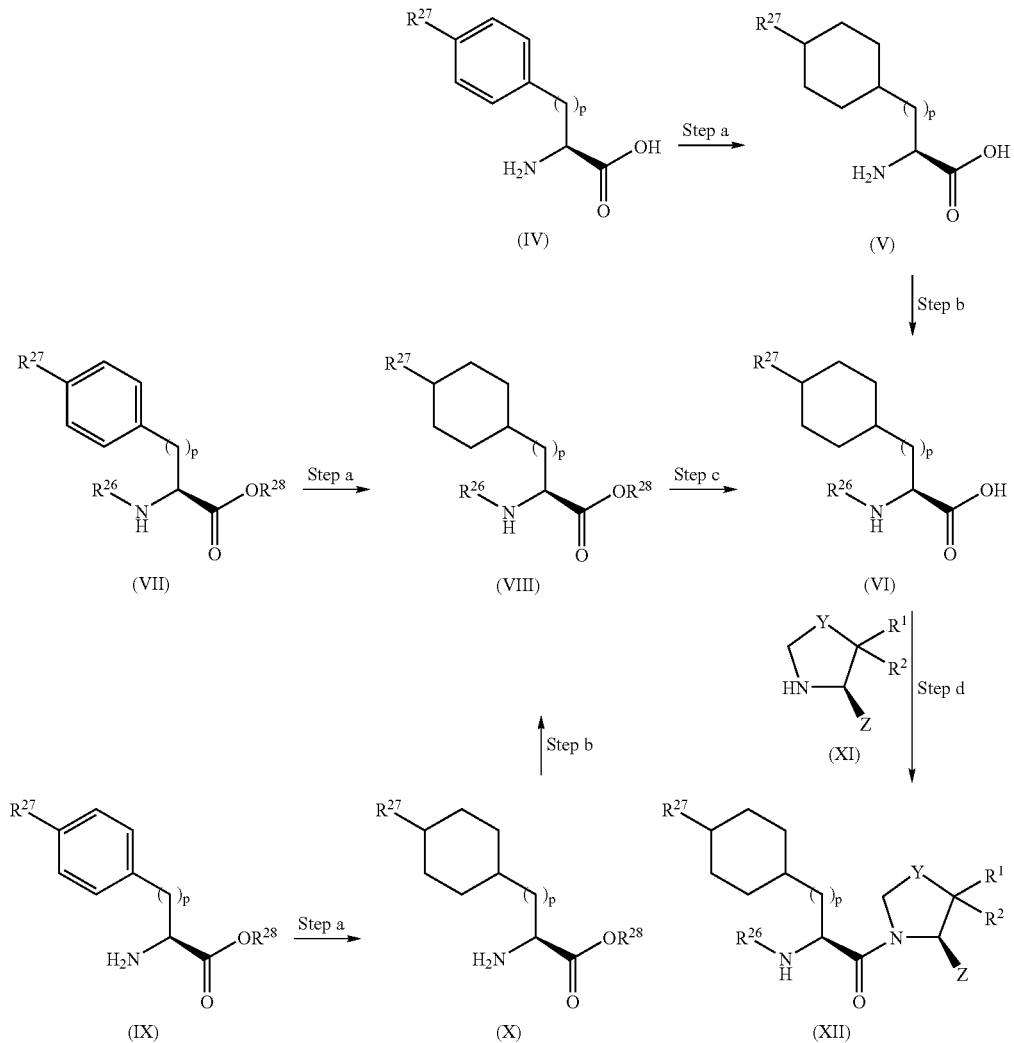

wherein $R^{26}$ is an amino acid-protecting group (e.g., tert-butoxycarbonyl (hereinafter to be referred to as Boc), benzyloxycarbonyl (hereinafter to be referred to as Cbz)), $R^{27}$ is a hydroxyl group or an amino group, $R^{28}$ is alkyl such as methyl, ethyl and the like, benzyl and the like, and other symbols are as defined above.

Step a: a step for producing a compound represented by the formula (V) or a salt thereof by reducing a compound represented by the formula (IV) or a salt thereof, producing a compound represented by the formula (VIII) or a salt thereof by reducing a compound represented by the formula (VII) or a salt thereof, or producing a compound represented by the formula (X) or a salt thereof by reducing a compound represented by the formula (IX) or a salt thereof.

The reaction is carried out by catalytic hydrogenation reaction using a metal catalyst. As the metal catalyst, palladium or oxide thereof, platinum or oxide thereof, rhodium or oxide thereof, ruthenium, Raney-nickel and the like are used, where these metals may be used in combination. In addition, the metal is supported on an inactive carrier such as activated carbon, alumina, barium sulfate, calcium carbonate and the like.

As the solvent to be used for the reaction, for example, alcohol solvent (e.g., methanol, ethanol etc.), hydrocarbon solvent (e.g., benzene, toluene, hexane, heptane etc.), ethyl acetate, acetic acid, water and the like can be mentioned and, where necessary, a mixed solvent thereof can be used.

The reaction is carried out under a hydrogen atmosphere at a normal pressure or high pressure, and the reaction temperature is about 0° C. to 150° C., preferably 0° C. to 120° C.

Step b: a step for producing a compound represented by the formula (VI) or a salt thereof by protecting an amino group of a compound represented by the formula (V) or a salt thereof, or producing a compound represented by the formula (VIII) or a salt thereof by protecting an amino group of a compound represented by the formula (X) or a salt thereof.

When $R^{26}$ is Boc, as a Boc agent, di-tert-butyl dicarbonate, 2-tert-butoxycarbonyloxyimino-2-phenylacetonitrile (Boc-ON), tert-butoxycarbonyl-4,6-dimethyl-2-thiopyrimidine and the like can be used. As the base to be used for this reaction, an organic base such as triethylamine, N,N-diisopropylethylamine (hereinafter to be referred to as DIPEA) and the like, hydroxide of alkali metal or alkaline earth metal (e.g., sodium hydroxide, potassium hydroxide etc.) and the like can be mentioned. As the solvent to be used for the reaction, for example, water, alcohol solvent (e.g., methanol, ethanol etc.), ether solvent (e.g., tetrahydrofuran (hereinafter to be referred to as THF), dioxane etc.) and the like, and, where necessary, a mixed solvent thereof can be used.

When $R^{26}$ is Cbz, as a Cbz agent, benzyloxycarbonyl chloride and the like can be used. In addition, an introduction method using an active ester such as dibenzyl dicarbonate, O-benzyloxycarbonyl-N-hydroxysuccinimide and the like can also be used. As the base to be used for this reaction, an organic base such as triethylamine, pyridine and the like, hydroxide of alkali metal or alkaline earth metal (e.g., sodium hydroxide, potassium hydroxide etc.), hydrogencarbonate of alkali metal or alkaline earth metal (e.g., sodium hydrogencarbonate, potassium hydrogencarbonate etc.) and the like can be mentioned. As the solvent to be used for the reaction, for example, water, ether solvent (e.g., THF, dioxane etc.), ethyl acetate, acetonitrile, N,N-dimethylformamide (hereinafter to be referred to as DMF) and the like can be mentioned and, where necessary, a mixed solvent thereof can be used.

Step c: a step for producing a compound represented by the formula (VI) or a salt thereof by deprotecting an ester-protected carboxyl group of a compound represented by the formula (VIII) or a salt thereof.

For the reaction, conventional deprotection reaction for carboxyl group can be used. As the base to be used, carbonate of alkali metal or alkaline earth metal (e.g., sodium carbonate, potassium carbonate etc.), hydroxide of alkali metal or alkaline earth metal (e.g., sodium hydroxide, potassium hydroxide etc.) and the like can be mentioned. When $R^{28}$ is a benzyl group, deprotection can also be carried out by a catalytic hydrogenation reaction using a metal catalyst such as platinum, palladium and the like. As the solvent to be used for the reaction, for example, alcohol solvent (e.g., methanol, ethanol etc.), ether solvent (e.g., THF, dioxane etc.) and the like can be mentioned and, where necessary, a mixed solvent with water can be mentioned. The reaction temperature therefor is about 0° C. to 100° C.

Step d: a step for producing a compound represented by the formula (XII) by reacting a compound represented by the formula (VI) or a salt thereof with a compound represented by the formula (XI) or a salt thereof.

It can be produced by reacting a compound represented by the formula (XI) or a salt thereof with an acidic compound represented by the formula (VI) or a reactive derivative thereof or a salt thereof using a dehydrating condensing agent in a solvent and, where necessary, in the presence of a base. As the reactive derivative of the acidic compound, acid anhydride, active ester (e.g., p-nitrophenyl ester, N-hydroxysuccinimido ester, pentafluorophenyl ester, 1-hydroxybenzotriazole ester etc.), acid halide (e.g., acid chloride, acid bromide etc.), imidazolide, mixed acid anhydride (e.g., anhydride with methyl carbonate, anhydride with ethyl carbonate etc.) and the like can be mentioned. As the solvent to be used, for example, ether solvent (e.g., diethyl ether, THF, dioxane etc.), hydrocarbon solvent (e.g., benzene, toluene, hexane, heptane etc.), halogen solvent (e.g., dichloromethane, dichloroethane, chloroform, carbon tetrachloride etc.), acetonitrile, DMF and the like can be mentioned. As the base to be used, an organic base such as triethylamine, 4-dimethylaminopyridine (hereinafter to be referred to as DMAP), DIPEA, triethylenediamine, 4-methylmorpholine and the like, carbonate of alkali metal or alkaline earth metal (e.g., sodium carbonate, potassium carbonate etc.), hydrogencarbonate of alkali metal or alkaline earth metal (e.g., sodium hydrogencarbonate, potassium hydrogencarbonate etc.), hydroxide of alkali metal or alkaline earth metal (e.g., sodium hydroxide, potassium hydroxide etc.) and the like can be mentioned.

As the dehydrating condensing agent, for example, condensing agents to be used for peptide synthesis, and the like can be mentioned. Specifically, for example, dicyclohexylcarbodiimide (hereinafter to be referred to as DCC), N-(3-dimethylaminopropyl)-N'-ethylcarbodiimide (hereinafter to be referred to as EDC) or hydrochloride thereof, 2-ethoxy-1-ethoxycarbonyl-1,2-dihydroxyquinoline, carbodiimidazole, diethylphosphoryl cyanide, benzotriazol-1-yloxytrispyrrolidinophosphonium hexafluorophosphate, diphenylphosphoryl azide (hereinafter to be referred to as DPPA), propanephosphinic anhydride, isobutyl chloroformate, diethylacetyl chloride, trimethylacetyl chloride and the like can be mentioned. These condensing agents are used alone or in combination with an activator such as N-hydroxysuccinimide, hydroxybenzotriazole (hereinafter to be referred to as HOBT), 3-hydroxy-4-oxo-3,4-dihydro-1,2,3-benzotriazine, DMAP and the like, preferably HOBT. The compound represented by the formula (XI) or a salt thereof is used in an amount of about 0.5 to 10 mol equivalents, preferably about 1 to 6 mol equivalents, and the condensing agent is used in an amount of about 0.5 to 10 mol equivalents, preferably about 1 to 5 mol equivalents, both per 1 mol of a compound represented by the formula (VI) or a salt thereof. The reaction temperature is about −30° C. to 100° C., preferably −10° C. to 80° C., and the reaction time is about 30 min to 96 hr, preferably 30 min to 48 hr.

Scheme 2 shows a production method of compound (I) wherein X═CH—$R^3$ and $R^3$═—$NR^7R^8$.

Scheme 2

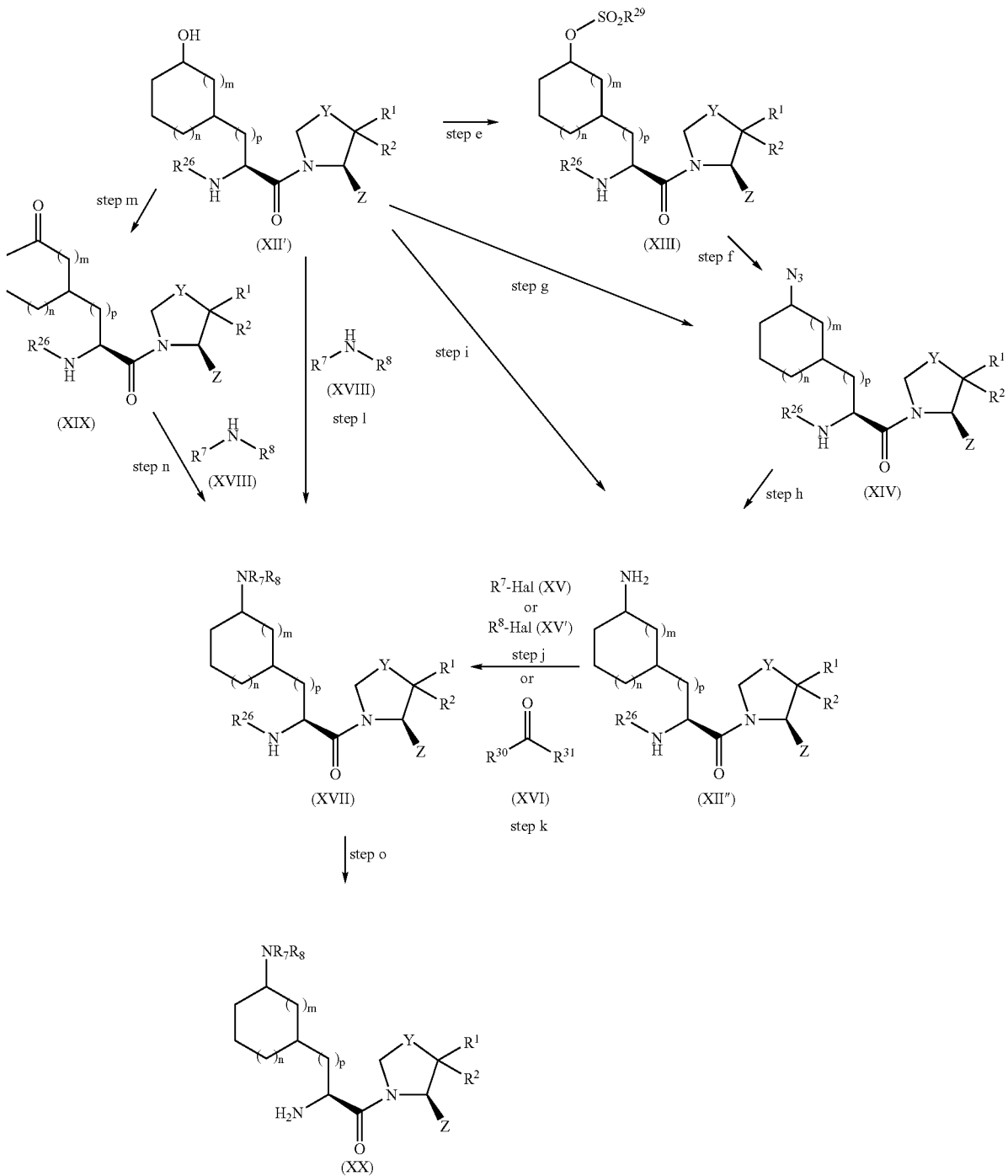

wherein $OSO_2R^{29}$ is a leaving group (e.g., p-toluenesulfonyloxy (OTs), methanesulfonyloxy (OMs), trifluoromethanesulfonyloxy (OTf)), Hal is a halogen atom, $R^{30}$ and $R^{31}$ are optionally the same or different and each independently is a hydrogen atom, alkyl, cycloalkyl, cycloalkylalkyl, aryl, arylalkyl, heteroaryl or heteroarylalkyl, or are optionally bonded to each other to form heterocycle having at least one nitrogen atom, and optionally having other further hetero atom(s), wherein the heterocycle is optionally substituted or condensed with an aromatic ring optionally having substituent(s), and other symbols are as defined above.

Step e: a step for producing a compound represented by the formula (XIII) by sulfonylating a hydroxyl group of a compound represented by the formula (XII').

This reaction can be carried out using a sulfonylating agent such as methanesulfonyl chloride, p-toluenesulfonyl chloride, trifluoromethanesulfonyl chloride and the like. In this event, a suitable base may be co-existent. As the base, an organic base such as triethylamine, DMAP, DIPEA, triethylenediamine, 4-methylmorpholine and the like, carbonate of alkali metal or alkaline earth metal (e.g., sodium carbonate, potassium carbonate etc.) and the like can be mentioned. As the solvent to be used for the reaction, for example, ether solvent (e.g., diethyl ether, THF, dioxane etc.), halogen solvent (e.g., dichloromethane, dichloroethane, chloroform, carbon tetrachloride etc.), DMF and the like can be mentioned. The reaction temperature is about −50° C. to 100° C., preferably −10° C. to 80° C., and the reaction time is about 0.1 to 96 hr, preferably 0.1 to 24 hr.

Step f: a step for producing a compound represented by the formula (XIV) by azidating a compound represented by the formula (XIII).

The reaction is carried out using a metal azide (e.g., sodium azide, lithium azide etc.). As the solvent to be used, for example, DMF, dimethyl sulfoxide (hereinafter to be referred to as DMSO), acetonitrile, dichloromethane, water and the like can be mentioned and, where necessary, a mixed solvent thereof can be used. As the additive, 18-crown-6 can also be used. The reaction temperature is about 0° C. to 120° C., and the reaction time is about 30 min to 24 hr.

Step g: a step for producing a compound represented by the formula (XIV) directly from a compound represented by the formula (XII').

The reaction is carried out by reaction with an azidating agent such as hydrogen azide, DPPA, zinc azide bispyridine complex and the like in the presence of phosphines such as triphenylphosphine, tributylphosphine and the like and azodicarboxylic acid diester. In addition, DPPA may be allowed to act in the presence of an organic base such as 1,8-diazabicyclo[5.4.0]-7-undecene (hereinafter to be referred to as DBU) and the like. As the solvent to be used, for example, ether solvent (e.g., diethyl ether, THF, dioxane etc.), hydrocarbon solvent (e.g., benzene, toluene, hexane, heptane etc.) and the like can be mentioned. The reaction temperature is about −30° C. to 100° C., and the reaction time is about 30 min to 72 hr.

Step h: a step for producing a compound represented by the formula (XII") or a salt thereof by reducing a compound represented by the formula (XIV).

As this reaction, a catalytic hydrogenation reaction using a metal catalyst such as palladium, platinum, nickel and the like, reduction by a metal hydride such as lithium aluminum hydride and the like, reduction using triphenylphosphine, thiol, sulfide, diborane or a transition metal, and the like can be mentioned, and preferably, a catalytic hydrogenation reaction using a metal catalyst and a reaction using triphenylphosphine can be mentioned.

Step i: a step for producing a compound represented by the formula (XII") or a salt thereof by phthalimidating a hydroxyl group of a compound represented by the formula (XII') or a salt thereof and then hydrolyzing the same.

In this reaction, phthalimide or a salt thereof (e.g., potassium salt etc.) is reacted in the presence of azodicarboxylic acid diesters (e.g., diethyl azodicarboxylate, diisopropyl azodicarboxylate etc.) and phosphines (e.g., triphenylphosphine, tributylphosphine etc.). The amount of the compound to be used is about 1 to 10 molar equivalents, preferably about 3 to 5 molar equivalents, of phthalimide or a salt thereof relative to the compound represented by the formula (XII') or a salt thereof. The amount of each of the azodicarboxylates and phosphines to be used is about 1 to 10 molar equivalents, preferably about 3 to 5 molar equivalents, relative to the compound represented by the formula (XII') or a salt thereof.

It is advantageous to use a solvent inert to the reaction. The solvent is not particularly limited as long as the reaction proceeds and, for example, ether solvent (e.g., diethyl ether, THF, dioxane etc.), hydrocarbon solvent (e.g., benzene, toluene, hexane, heptane etc.), halogen solvent (e.g., dichloromethane, dichloroethane, chloroform etc.), acetonitrile, DMF and the like can be mentioned and, where necessary, a mixed solvent thereof can be used.

The phthalimide compound thus produced can be led to a compound represented by the formula (XII") or a salt thereof by hydrolysis using hydrazine. As the solvent to be used for the reaction, for example, water, alcohol solvent (e.g., methanol, ethanol etc.), ether solvent (e.g., THF, dioxane etc.) and the like can be mentioned and, where necessary, a mixed solvent thereof can be used.

Step j: a step for producing a compound represented by the formula (XVII) or a salt thereof by reacting a compound represented by the formula (XII") or a salt thereof with a compound represented by the formula (XV) or a compound represented by (XV').

The reaction is carried out in the presence of an organic base such as triethylamine, DIPEA and the like, preferably DIPEA, in a solvent inert to the reaction such as N-methyl-2-pyrrolidone, DMF, THF and the like, at 0° C. to a temperature near the boiling point of the solvent, preferably 0° C. to 80° C.

Step k: a step for producing a compound represented by the formula (XVII) or a salt thereof by reacting a compound represented by the formula (XII") or a salt thereof with a compound represented by the formula (XVI), followed by reduction.

The reductive amination reaction can be carried out, for example, by reacting a compound represented by the formula (XII") or a salt thereof with a compound represented by the formula (XVI) in a solvent such as ether solvent (e.g., diethyl ether, THF, dioxane etc.), hydrocarbon solvent (e.g., benzene, toluene, hexane, heptane etc.), halogen solvent (e.g., dichloromethane, dichloroethane, chloroform, carbon tetrachloride etc.), alcohol solvent (e.g., methanol, ethanol, n-propanol, isopropanol etc.), acetonitrile, DMF and the like, or in a mixed solvent thereof as necessary, in the presence of a metal hydride complex compound (e.g., composite hydride compound such as sodium borohydride, sodium cyanoborohydride, sodium triacetoxyborohydride and the like, diborane etc.) and, where necessary, an acidic catalyst (e.g., acetic acid, p-toluenesulfonic acid, boron trifluoride diethyl ether complex etc.). The compound represented by the formula (XVI) is used in an amount of about 0.5 to 10 molar equivalents, preferably about 1 to 5 molar equivalents, and the metal hydride complex compound is used in an amount of about 0.5 to 10 molar equivalents, preferably about 1 to 5 molar equivalents, both relative to a compound represented by the formula (XII") or a salt thereof. The reaction temperature is −20° C. to 200° C., preferably 0° C. to 100° C., and the reaction time is about 0.5 to 96 hr, preferably 0.5 to 24 hr.

A compound represented by the formula (XVII) wherein $R^7$ and $R^8$ are the same or different or a salt thereof can be produced by repeating Step j or k as necessary.

Step l: a step for producing a compound represented by the formula (XVII) or a salt thereof by activating a compound represented by the formula (XII') and then reacting the compound with an amine represented by the formula (XVIII) or a salt thereof.

The compound represented by the formula (XII') or a salt thereof can be activated with about 1 to 10 molar equivalents, preferably about 1 to 5 molar equivalents, of a halogenating reagent such as thionyl chloride, phosphorus trichloride, phosphorus pentachloride, phosphorus tribromide, phosphorus pentabromide, carbon tetrabromide-triphenylphosphine and the like in a solvent, or with about 1 to 10 molar equivalents, preferably about 1 to 5 molar equivalents, of p-toluenesulfonyl chloride, methanesulfonyl chloride, trifluoromethanesulfonic anhydride and the like in the presence of a base [organic base such as triethylamine, DMAP, DIPEA, triethylenediamine, 4-methylmorpholine and the like, carbonate of alkali metal or alkaline earth metal (e.g., sodium carbonate, potassium carbonate etc.), hydrogencarbonate of alkali metal or alkaline earth metal (e.g., sodium hydrogencarbonate, potassium hydrogencarbonate etc.) and the like. The solvent used here is, for example, acetonitrile, halogen solvent (e.g., dichloromethane, dichloroethane, chloroform etc.), ether solvent (e.g., diethyl ether, THF, dioxane etc.), hydrocarbon solvent (e.g., benzene, toluene, hexane, heptane etc.) and the like, and the reaction temperature is about −20° C. to 100° C., preferably about 0° C. to 60° C. The activated compound or a salt thereof may be reacted with potassium iodide, sodium iodide and the like in a solvent such as acetonitrile, DMF and the like to give an iodide. The compound thus activated or a salt thereof is reacted with about 1 to 10 molar equivalents, preferably about 1 to 5 molar equivalents, of an amine represented by the formula (XVIII) or a salt thereof in a solvent to give a compound represented by the formula (XVII) or a salt thereof. The solvent used here is, for example, acetonitrile, halogen solvent (e.g., dichloromethane, dichloroethane, chloroform etc.), ether solvent (e.g., diethyl ether, THF, dioxane etc.), hydrocarbon solvent (e.g., benzene, toluene, hexane, heptane etc.), DMF, N,N-dimethylacetamide and the like, and the reaction temperature is about −20° C. to 150° C., preferably about 0° C. to 100° C. Where necessary, a base [organic base such as triethylamine, DMAP, DIPEA, triethylenediamine, 4-methylmorpholine and the like, carbonate of alkali metal or alkaline earth metal (e.g., sodium carbonate, potassium carbonate etc.), hydrogencarbonate of alkali metal or alkaline earth metal (e.g., sodium hydrogencarbonate, potassium hydrogencarbonate etc.) and the like] may be used.

In addition, a compound represented by the formula (XII') and an amine represented by the formula (XVIII) or a salt thereof may be subjected to Mitsunobu reaction or a modification thereof to give a compound represented by (XVII) or a salt thereof. This reaction is carried out in the presence of azodicarboxylic acid diesters (e.g., diethyl azodicarboxylate, 1,1'-(azodicarbonyl)dipiperidines) and phosphines (e.g., triphenylphosphine, tributylphosphine etc.). The amount of the compound to be used is about 1 to 5 molar equivalents, preferably about 1 to 2 molar equivalents, of an amine represented by the formula (XVIII) or a salt thereof relative to the compound represented by the formula (XII') or a salt thereof. The amount of each of the azodicarboxylic acid diesters and phosphines to be used is about 1 to 5 molar equivalents, preferably about 1 to 2 molar equivalents, relative to the compound represented by the formula (XII') or a salt thereof. It is advantageous to use a solvent inert to the reaction. The solvent is not particularly limited as long as the reaction proceeds and, for example, ether solvent (e.g., diethyl ether, THF, dioxane etc.), hydrocarbon solvent (e.g., benzene, toluene, hexane, heptane etc.), halogen solvent (e.g., dichloromethane, dichloroethane, chloroform etc.), acetonitrile, DMF and the like can be mentioned.

Step m: a step for producing a compound represented by the formula (XIX) by oxidizing a compound represented by the formula (XII').

Examples of the oxidization reaction include a method using an oxidant such as pyridinium chlorochromate, pyridinium dichromate, manganese dioxide and the like, and DMSO oxidation such as DMSO-oxalyl chloride, DMSO-acetic anhydride, DMSO-trifluoroacetic anhydride, DMSO-pyridine sulfur trioxide complex and DMSO-DCC, -EDC and the like using dichloroacetic acid as a catalyst. As the solvent, halogen solvent (e.g., dichloromethane, dichloroethane, chloroform etc.), ether solvent (e.g., diethyl ether, THF, dioxane etc.), DMF and the like can be mentioned. In addition, a method comprising reaction with an aqueous sodium hypochlorite solution using 2,2,6,6-tetramethyl-1-piperidinyloxy free radical as a catalyst in the presence of sodium bromide in ethyl acetate or toluene, and the like can be mentioned. By the reaction with 1 to 10 molar equivalents, preferably 1 to 3 molar equivalents, of an oxidant and the like, a compound represented by the formula (XIX) or a salt thereof can be obtained. The reaction temperature is about −78° C. to 100° C., preferably −40° C. to 60° C., and the reaction time is about 30 min to 24 hr, preferably about 1 to 15 hr.

Step n is performed in the same manner as in Step k.

Step o: a step for producing a compound represented by the formula (XX) or a salt thereof by deprotecting a compound represented by the formula (XVII) or a salt thereof.

In this reaction, when the protecting group $R^{26}$ is a Boc group, deprotection can be performed using an acid such as hydrochloric acid, sulfuric acid, trifluoroacetic acid, p-toluenesulfonic acid, methanesulfonic acid and the like. In this case, these acids are dissolved in an organic solvent or water and the deprotection can be carried out at about −50° C. to 50° C. This reaction can be carried out, for example, in a solvent such as ether solvent (e.g., THF, dioxane etc.), halogen solvent (e.g., dichloromethane, dichloroethane, chloroform etc.), alcohol solvent (e.g., methanol, ethanol etc.), acetonitrile, ethyl acetate and the like. When the protecting group $R^{26}$ is a Cbz group, deprotection can be performed with an acid, or by a catalytic hydrogenation reaction using a metal catalyst such as palladium and the like. The catalytic hydrogenation reaction can be carried out in a solvent such as ether solvent (e.g., THF, dioxane etc.), alcohol solvent (e.g., methanol, ethanol etc.), ethyl acetate and the like. The reaction temperature is about 0° C. to 100° C. and a hydrogen gas can also be used at normal pressure or under pressurization, or a combination of reagents such as formic acid-ammonium formate can also be used. The reaction using an acid may be a reaction with hydrobromic acid-acetic acid, or can be carried out using, for example, trifluoroacetic acid or trifluoromethanesulfonic acid, preferably trifluoromethanesulfonic acid, in, where necessary, a solvent inert to the deprotection reaction such as halogen solvent (e.g., dichloromethane, dichloroethane, chloroform etc.) and the like in the presence of thioanisole or anisole.

Compound (XX) obtained here can be taken out as a base or a salt with a suitable acid. The suitable acid includes, for example, hydrochloric acid, sulfuric acid, trifluoroacetic acid, p-toluenesulfonic acid, methanesulfonic acid, acetic acid and the like.

Scheme 3 shows a production method of compound (I) wherein X=CH—$R^3$, and $R^3$=—$NR^9COR^{10}$.

17

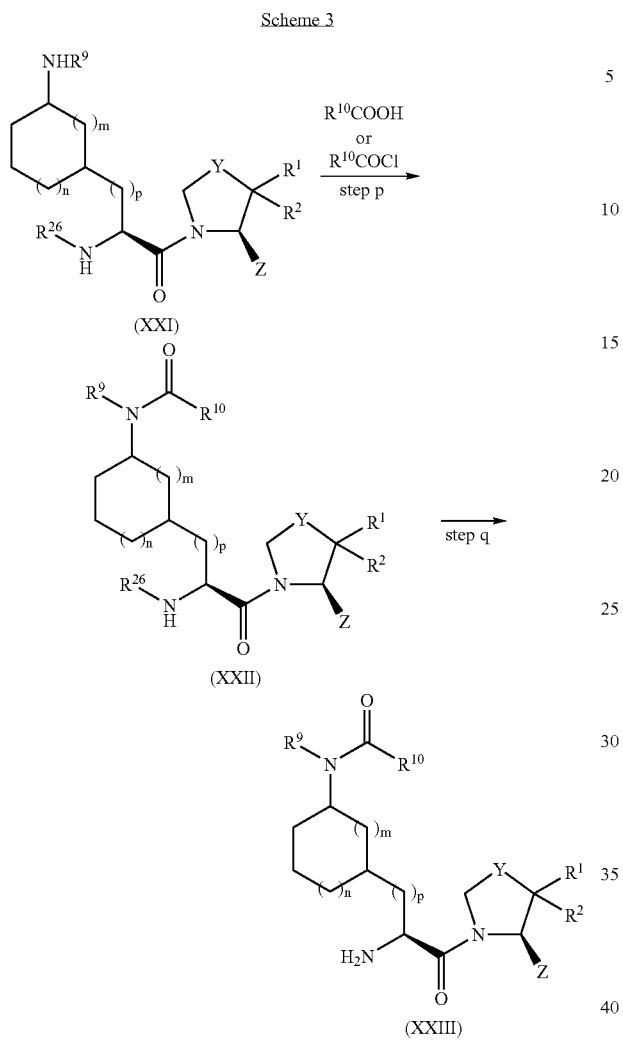

wherein each symbol is as defined above.

A compound represented by the formula (XXI) or a salt thereof is the same as the compound represented by the formula (XII″) obtained in Scheme 2 or a salt thereof, or a compound represented by the formula (XVII) wherein one of $R^7$ and $R^8$ is a hydrogen atom or a salt thereof.

Step p: a step for producing an amide compound represented by the formula (XXII) or a salt thereof by acylating a compound represented by the formula (XXI) or a salt thereof.

The reaction is carried out using $R^{10}COCl$ or by converting $R^{10}CO_2H$ to an acid halide with thionyl chloride, thionyl bromide and the like, or to a mixed acid anhydride with pivaloyl chloride, isobutyl chloroformate and the like. As the base to be used for the reaction, an organic base such as triethylamine, DMAP, DIPEA, triethylenediamine, 4-methylmorpholine and the like can be mentioned, and as the solvent to be used, for example, ether solvent (e.g., diethyl ether, THF, dioxane etc.), hydrocarbon solvent (e.g., benzene, toluene, hexane etc.), halogen solvent (e.g., dichloromethane, dichloroethane, chloroform etc.), ethyl acetate, chloroform, DMF, DMSO, hexamethylphosphoramide and the like can be mentioned. This reaction is generally carried out at about 0° C. to 120° C. for about 10 min to 10 hr.

The reaction with $R^{10}CO_2H$ can be carried out under the conditions shown in Scheme 1, Step d.

18

Step q is performed in the same manner as in Scheme 2, Step o.

Scheme 4 shows a production method of compound (I) wherein $X=CH-R^3$ and $R^3=-NR^{11}CONR^{12}R^{13}$.

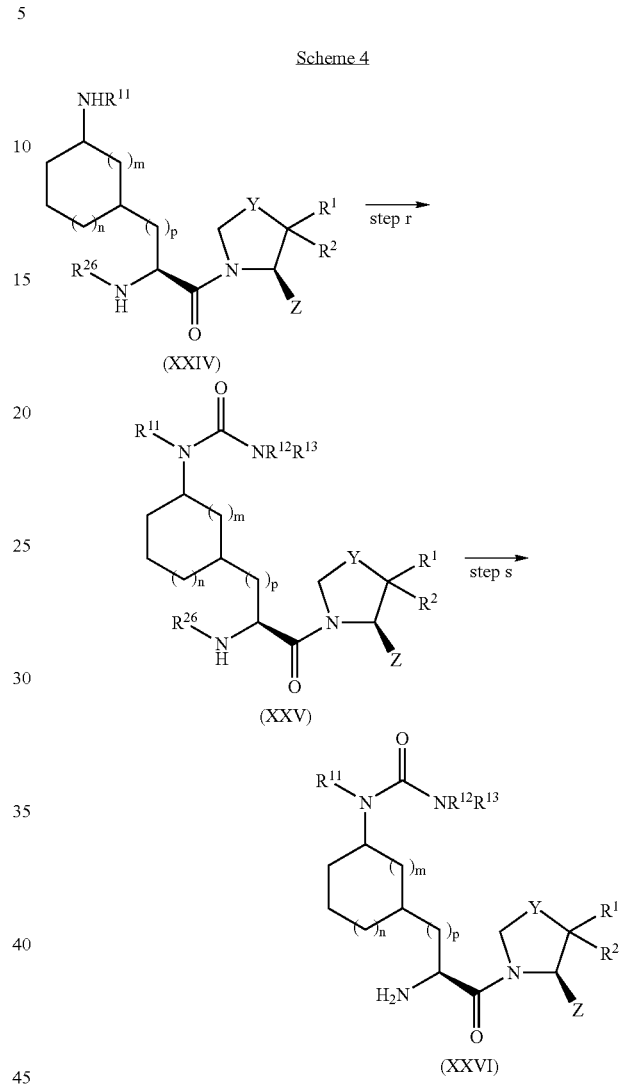

wherein each symbol is as defined above.

A compound represented by the formula (XXIV) is the same as the compound represented by the formula (XII″) obtained in Scheme 2 or a salt thereof, or a compound represented by the formula (XVII) wherein one of $R^7$ and $R^8$ is a hydrogen atom or a salt thereof.

Step s: a step for producing a urea compound represented by the formula (XXV) by reacting a compound represented by the formula (XXIV) or a salt thereof.

The reaction can be carried out using isocyanate such as $R^{12}$—NCO and the like. The reaction is carried out in a solvent inert to the reaction such as toluene, chloroform, dichloromethane, THF and the like generally at a temperature of −20° C. to 80° C., preferably 0° C. to 25° C.

In addition, for example, a method using carbodiimidazole, phosgene, diphosgene (trichloromethyl chloroformate) or triphosgene [bis(trichloromethyl)carbonate] and the like with an amine represented by $R^{12}R^{13}NH$ and a tertiary organic base such as triethylamine and the like may be employed.

Step s is performed in the same manner as in Scheme 2, Step o.

Scheme 5 shows a production method of compound (I) wherein X=CH—$R^3$ and $R^3$=—$NR^{14}SO_2R^{15}$.

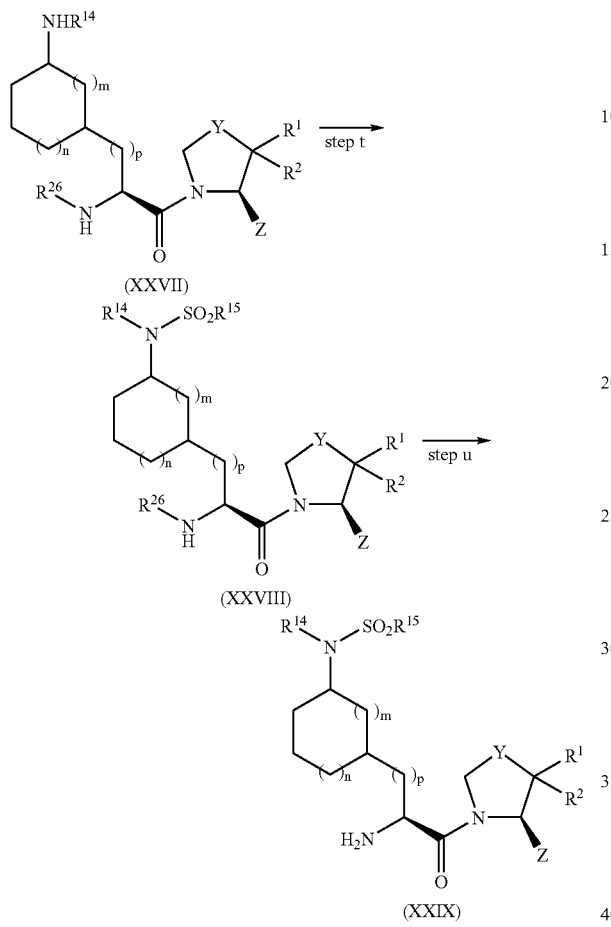

chloride, which is then reacted with an aryl compound in the presence of a Lewis acid such as aluminum chloride and the like may be employed.

Step u is performed in the same manner as in Scheme 2, Step o.

Scheme 6 shows a different production method of a compound represented by the formula (XVII) or a salt thereof. This production method is useful for a compound wherein both $R^7$ and $R^8$ are not hydrogen atoms.

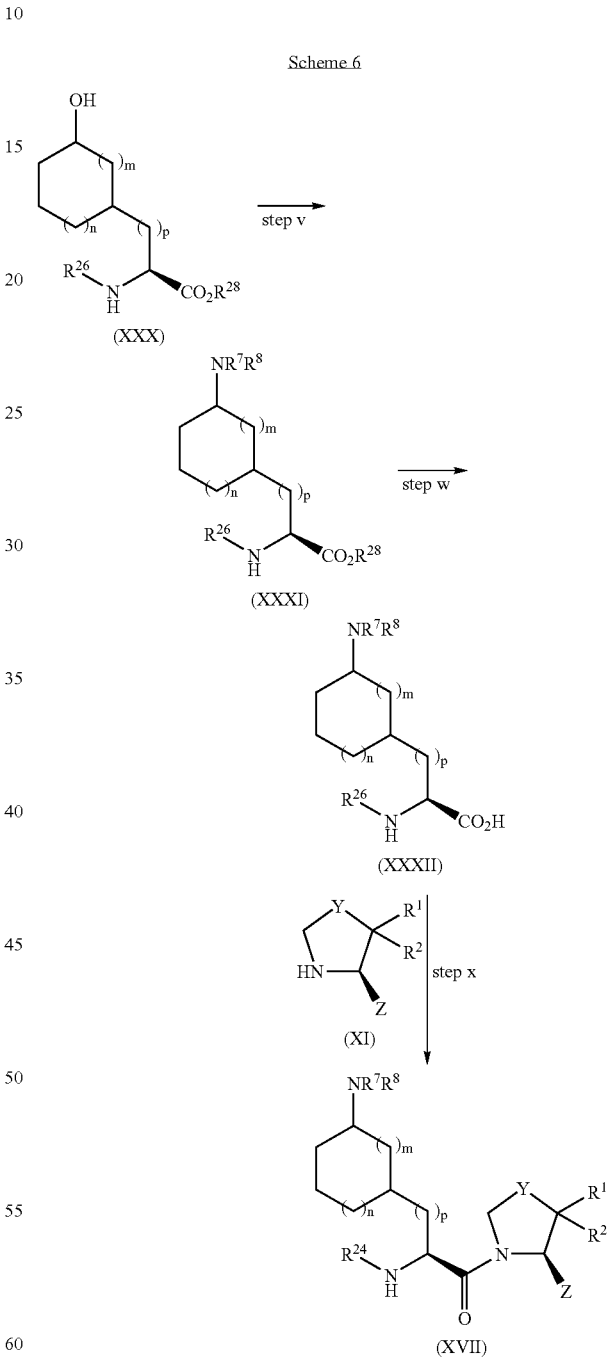

wherein each symbol is as defined above.

The compound represented by the formula (XXVII) or a salt thereof is the same as the compound represented by the formula (XII'') obtained in Scheme 2 or a salt thereof, or a compound represented by the formula (XVII) wherein one of $R^7$ and $R^8$ is a hydrogen atom or a salt thereof.

Step t: a step for producing a sulfonamide compound represented by the formula (XXVIII) by sulfonylating a compound represented by the formula (XXVII) or a salt thereof.

The reaction is carried out using sulfonyl chloride such as $R^{15}$—$SO_2Cl$ and the like in the presence of an organic base such as triethylamine, pyridine and the like or an inorganic base such as carbonate of alkali metal or alkaline earth metal (e.g., sodium carbonate, potassium carbonate etc.), hydroxide of alkali metal or alkaline earth metal (e.g., sodium hydroxide, potassium hydroxide etc.) and the like in a solvent inert to the reaction such as water, toluene, chloroform, dichloromethane, THF and the like generally at a temperature of about −20° C. to 80° C.

Alternatively, a method comprising reacting a compound represented by the formula (XXVII) with sulfuryl chloride in the presence of a tertiary organic base such as triethylamine and the like in a solvent inert to the reaction such as chloroform, dichloromethane, THF and the like to give sulfamoyl wherein each symbol is as defined above.

Step v is the same as the conversion method of the compound represented by the formula (XII') to a compound represented by the formula (XVII) or a salt thereof, as shown in Scheme 2.

Step w is performed in the same manner as in Scheme 1, Step c.

Step x is performed in the same manner as in Scheme 1, Step d.

The compound represented by the formula (XXIII) as shown in Scheme 3, the compound represented by the formula (XXVI) as shown in Scheme 4, and a compound represented by the formula (XXIX) as shown in Scheme 5 can be produced by the route shown in Scheme 6.

Scheme 7 shows a production method of compound (I) wherein X=N—R⁴.

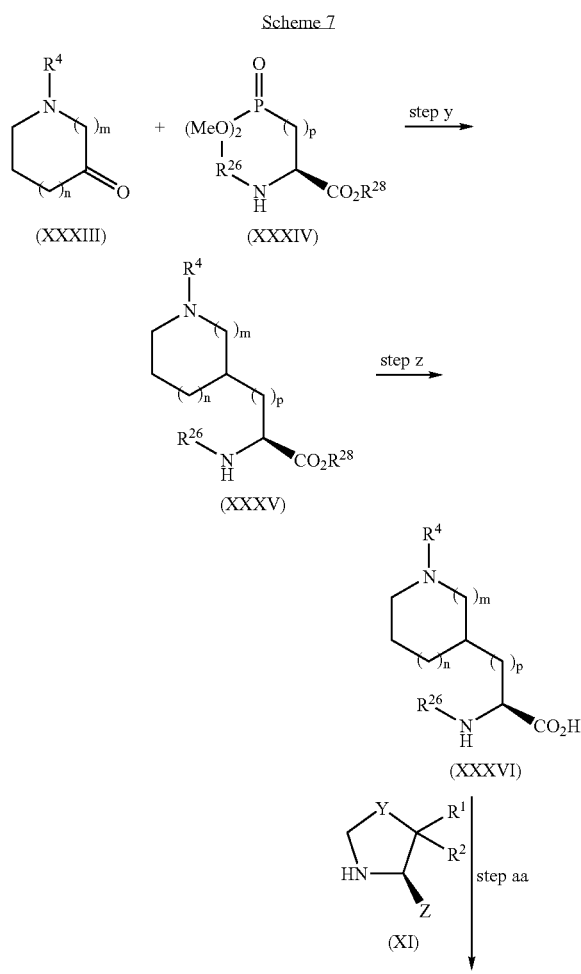

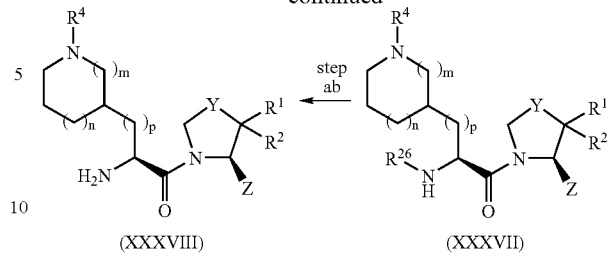

wherein each symbol is the as defined above.

Step y: a step for producing a compound represented by the formula (XXXV) or a salt thereof by reacting a compound represented by the formula (XXXIII) and a compound represented by the formula (XXXIV), followed by reduction.

A coupling reaction between a compound represented by the formula (XXXIII) and a compound represented by the formula (XXXIV) is carried out in the presence of a bulky organic base such as DBU, DIPEA, potassium tert-butoxide and the like in a solvent inert to the reaction such as chloroform, dichloromethane, THF, acetonitrile and the like. As the additive, lithium chloride or 18-crown-6 can also be used. The reaction temperature is about −80° C. to 80° C., preferably −80° C. to 25° C., and the reaction time is about 1 to 72 hr, preferably 1 to 24 hr.

The unsaturated compound thus obtained is subjected to a catalytic hydrogenation reaction using a transition metal catalyst to reduce the carbon-carbon double bond. As the transition metal catalyst to be used, for example, palladium catalyst [for example, palladium carbon, tetrakis(triphenylphosphine)palladium, dichloro bis(triphenylphosphine)palladium, palladium oxide etc.] can be mentioned. The catalytic hydrogenation reaction is carried out in a solvent such as alcohol solvent (e.g., methanol, ethanol etc.), acetic acid and the like, and a catalytic amount of an inorganic acid such as hydrochloric acid and the like may be added. This reaction is carried out using a hydrogen gas at normal pressure or under pressurization at a reaction temperature of about 0° C. to 100° C. In addition, the enantioselective catalytic hydrogenation reaction of the unsaturated compound can be carried out by the method of Burk et al. [Burk et al., J. Am. Chem. Soc., vol. 117, 9375-9376 (1995)].

Step z is performed in the same manner as in Scheme 1, Step c.

Step aa is performed in the same manner as in Scheme 1, Step c.

Step ab is performed in the same manner as in Scheme 2, Step o.

Scheme 8 shows a different production method of a compound represented by the formula (XXXVI) or a salt thereof.

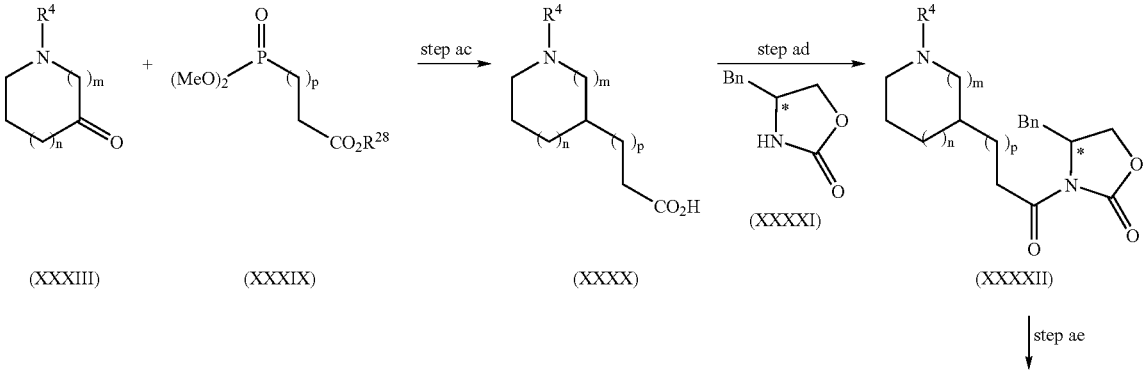

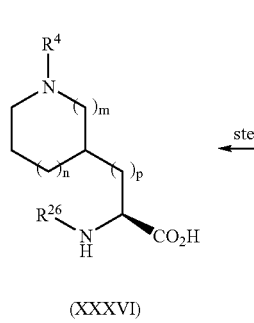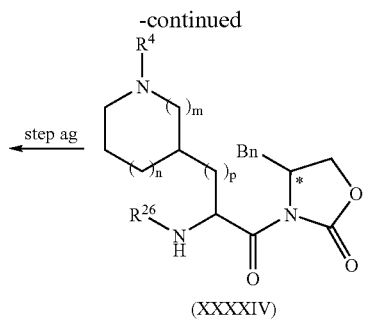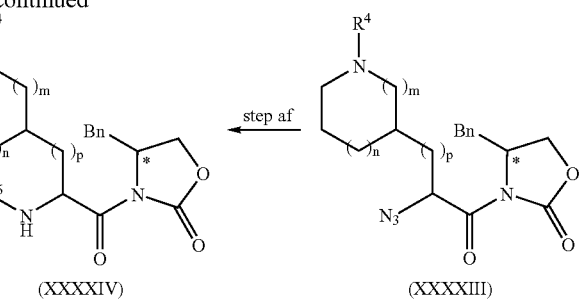

wherein each symbol is as defined above.

Step ac is performed in the same manner as in Scheme 7, Step y and Scheme 1, Step c.

Step ad: a step for producing a compound represented by the formula (XXXXII) or a salt thereof by condensation reacting a compound represented by the formula (XXXX) or a salt thereof with a chiral auxiliary group represented by the formula (XXXXI).

According to this method, a carboxyl group of a compound represented by the formula (XXXX) or a salt thereof is activated and the compound is reacted with a chiral auxiliary group represented by the formula (XXXXI). The carboxyl group can be activated, for example, by reacting with thionyl chloride or acid chloride such as pivaloyl chloride and the like in the presence of an organic base such as triethylamine and the like. The reaction is carried out in a solvent inert to the reaction such as THF and the like. Lithium chloride is added to the carboxyl group thus activated and reacted therewith a chiral auxiliary group represented by the formula (XXXXI). The reaction temperature is about −80° C. to 80° C., preferably −80° C. to 30° C., and the reaction time is about 1 to 72 hr, preferably 1 to 24 hr.

Step ae: a step for producing a compound represented by the formula (XXXXIII) or a salt thereof by azidation reacting a compound represented by the formula (XXXXII) or a salt thereof.

The stereoselective azidation reaction can be carried out by the method of Evans et al. [Evans et al., J. Am. Chem. Soc., vol. 112, 4011-4030 (1990)]. For example, a compound represented by the formula (XXXXII) or a salt thereof is converted to an enolate thereof salt with an alkali metal base such as potassium bis(trimethylsilyl)amide and the like in a solvent inert to the reaction such as THF and the like, which is then reacted with 2,4,6-triisopropylbenzenesulfonyl azide and treated with acetic acid to give an azide compound. The reaction temperature is about −80° C. to 80° C., preferably −80° C. to 30° C., and the reaction time is about 1 to 72 hr, preferably 1 to 24 hr.

Step af is performed in the same manner as in Scheme 2, Step h and Scheme 1, Step b.

Step ag: a step for producing a compound represented by the formula (XXXVI) or a salt thereof by hydrolyzing a compound represented by the formula (XXXXIV) or a salt thereof.

Oxazolidinone can be hydrolyzed with a base such as lithium hydroxide aqueous solution and the like. As the solvent to be used, for example, alcohol solvent (e.g., methanol, ethanol etc.), ether solvent (e.g., THF, dioxane etc.), or, where necessary, a mixed solvent thereof can be used. The reaction temperature is about 0° C. to 100° C.

While a method using a chiral auxiliary group represented by the formula (XXXXI) has been shown here, other chiral auxiliary groups can also be used according to the method of Ho et al. [J. Org. Chem., vol. 60, 2271-2273 (1995)].

In addition, a compound represented by the formula (XXXVIII) can also be produced by hydrolyzing oxazolidinone of a compound represented by the formula (XXXXIII) or a salt thereof, condensing with a compound represented by the formula (XI) or a salt thereof and converting an azido group to an amino group.

The α-amino acid derivative of the formula (I) of the present invention produced in this manner can be obtained at an optional purity by applying a known separation and purification means as necessary, such as concentration, extraction, chromatography, reprecipitation, recrystallization and the like.

The α-amino acid derivative of the formula (I) can be prepared into an acid addition salt as necessary with an inorganic acid such as hydrochloric acid, hydrobromic acid, hydriodic acid, sulfuric acid, phosphoric acid and the like, an organic acid such as methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like, or an amino acid such as glutamic acid, asparagine acid and the like. In addition, it is also present as a solvate such as hydrate and the like.

The compound represented by the formula (I) or a pharmacologically acceptable salt of the present invention has a superior DPP-IV inhibitory action in mammals (e.g., human, monkey, dog, cat, rat and the like).

Therefore, the compound represented by the formula (I) and a pharmacologically acceptable salt thereof of the present invention are useful as DPP-IV inhibitors and useful for the prophylaxis or treatment of various diseases relating to DPP-IV inhibitors, for example, for the prophylaxis or treatment of diseases where GLP-1 is considered to be related (e.g., diabetes, obesity and the like), and the like.

The compound represented by the formula (I) of the present invention can be administered to the same subject together with other therapeutic drug for diabetes, therapeutic drug for diabetic complications, anti-hyperlipidemic agent, antihypertensive agent and the like at the same time or time lag. As used herein, examples of the therapeutic drug for diabetes include insulin sensitivity increasing agent, α-glucosidase inhibitor, biguanide agent and the like. Examples of the therapeutic drug for diabetic complications include aldose reductase therapeutic agent. As the anti-hyperlipidemic agent, statin compound, which is a cholesterol synthetase inhibitor, squalene synthetase inhibitor, fibrates having triglyceride lowering action, and the like can be mentioned. As the antihypertensive agent, calcium antagonist, angiotensin converting enzyme inhibitor, angiotensin II antagonist and the like can be mentioned.

When the compound of the present invention is used on combination with multiple agents, the mixing ratio thereof can be appropriately determined depending on the subject of administration, age and body weight of the administration subject, symptom, administration time, dosage form, administration method, combination and the like.

When the compound represented by the formula (I) or an acid addition salt thereof of the present invention is used as the aforementioned pharmaceutical agent, it is used on its own or admixed with an appropriate pharmacologically acceptable carrier, an excipient, a diluent and the like, and administered orally or parenterally in the form of powder, granule, tablet, capsule, injection and the like. The abovementioned preparation contains an effective amount of a compound represented by the formula (I) or a pharmacologically acceptable salt thereof.

While the dose of a compound represented by the formula (I) or a pharmacologically acceptable salt thereof varies depending on the administration route, target disease, symptom, body weight and age of patients, and the compound to be used, it can be determined as appropriately according to the administration object. Generally, when orally administered to an adult, 0.01-1000 mg/kg body weight/day, preferably 0.05-500 mg/kg body weight/day, is preferably administered once a day or in several doses a day.

The present invention is explained in detail by referring to Reference Examples and Examples, which are not to be construed as limitative.

$^1$H-NMR was measured at 300 MHz. The chemical shift of $^1$H-NMR relative delta ($\delta$) value was expressed in parts per million (ppm) using tetramethylsilane (TMS) as the internal standard. For the coupling constant, obvious multiplicity is shown in hertz (Hz) using s (singlet), d (doublet), t (triplet), m (multiplet), dd (doublet of doublets), brs (broad singlet) and the like. Thin-layer chromatography used was manufactured by Merck, and column chromatography was carried out using silica gel manufactured by Fuji silysia chemical.

For drying organic solutions in extraction, anhydrous sodium sulfate or anhydrous magnesium sulfate was used, unless particularly indicated.

The piperazine compounds and piperidine compound, which are the starting materials shown in Examples, were synthesized by the method described in WO02/14271.

EXAMPLE 1

3-((S)-2-amino-2-{trans-4-[4-(5-cyano-2-pyridinyl)-1-piperazinyl]-1-cyclohexyl}acetyl)-1,3-thiazolidine

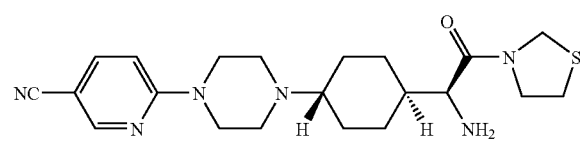

(1) 4-Hydroxy-L-phenylglycine (21.56 g) was dissolved in water (250 mL) and 3 mol/L aqueous sodium hydroxide solution (43 mL). Raney-nickel (130 g) was added to conduct hydrogenation reaction under heating at 80° C. and 7.0 kgf/cm². After 3 hr, the reaction mixture was filtered, and the solid was washed with water. The filtrate was concentrated under reduced pressure to 200 mL. 1,4-Dioxane (150 mL) and triethylamine (32 mL) were added to the concentrated solution, di-tert-butyl dicarbonate (33.8 g) was added under ice-cooling, and the mixture was stirred at room temperature for 20 hr. The organic solvent was evaporated from the reaction mixture, and 2 mol/L hydrochloric acid (155 mL) was poured thereinto under icecooling to adjust the mixture to pH 2. Sodium chloride was added to saturation and the mixture was extracted 4 times with ethyl acetate. The extract was dried and concentrated under reduced pressure. THF (350 mL) and 1,3-thiazolidine (13.8 g) were added to the residue, HOBT (30.40 g) and EDC hydrochloride (29.7 g) were successively added under ice-cooling, and the mixture was stirred at room temperature for 12 hr. The reaction mixture was concentrated, and saturated aqueous sodium hydrogencarbonate solution was added to the concentrate. The mixture was extracted with chloroform and the extract was dried. The solvent was evaporated under reduced pressure and the residue was purified by silica gel chromatography to give 3-[(S)-2-tert-butoxycarbonylamino-3-(4-hydroxy-1-cyclohexyl)acetyl]-1,3-thiazolidine (41.66 g, yield 93.8%) as a white solid.

(2) The above-mentioned compound (32.98 g) was dissolved in DIPEA (70 mL), dichloromethane (70 mL) and DMSO (270 mL). While maintaining the liquid temperature at 20° C., pyridine sulfur trioxide complex (25.93 g) was added and the mixture was stirred for 3 hr. Under ice-cooling, 10% citric acid aqueous solution was added to the reaction mixture, and the mixture was extracted with toluene. The extract was washed with water and saturated brine and dried. The solvent was evaporated under reduced pressure and the residue was purified by silica gel chromatography to give 3-[(S)-2-tert-butoxycarbonylamino-2-(4-oxo-1-cyclohexyl)acetyl]-1,3-thiazolidine (22.10 g, yield 67.4%) as a colorless highly viscose oil.

$^1$H-NMR (CDCl$_3$) $\delta$ 1.43 (9H, s), 1.48-1.68 (2H, m), 1.95-2.18 (3H, m), 2.25-2.50 (4H, m), 3.04 (1H, t, J=6.3 Hz), 3.12 (1H, t, J=6.3 Hz), 3.70-4.12 (2H, m), 4.38-4.78 (3H, m), 5.29 (1H, d, J=9.2 Hz).

(3) The above-mentioned compound (630 mg) and 1-(5-cyano-2-pyridyl)piperazine (381 mg) were dissolved in chloroform (8 mL), sodium triacetoxyborohydride (780 mg) was added, and the mixture was stirred at room temperature for 22 hr. Saturated aqueous sodium hydrogencarbonate solution was added to the reaction mixture, and the mixture was extracted with chloroform. The extract was washed with saturated brine and dried. The solvent was evaporated under reduced pressure and the residue was purified by silica gel chromatography to give 3-((S)-2-tertbutoxycarbonylamino-2-{trans-4-[4-(5-cyano-2-pyridyl)-1-piperazinyl]-1-cyclohexyl}acetyl)-1,3-thiazolidine as a pale-yellow amorphous trans form (604 mg, yield 63.8%), and a white amorphous cis form (344 mg, yield 36.2%).

(4) The above-mentioned trans form (596 mg) was dissolved in dichloromethane (5 mL), trifluoroacetic acid (10 mL) was added under ice-cooling, and the mixture was stirred for 3 hr. The reaction mixture was concentrated under reduced pressure, saturated aqueous sodium hydrogencarbonate solution was added to the residue, and the mixture was extracted with chloroform. The extract was washed with saturated brine and dried. The solvent was evaporated under reduced pressure, and the residue was purified by silica gel chromatography and crystallized from ethyl acetate to give the title compound (270 mg, yield 56.1%) as a white powder.

¹H-NMR (CDCl₃) δ 1.38-1.95 (9H, m), 2.18-2.25 (1H, m), 2.50-2.62 (4H, m), 3.02 (1H, t, J=6.5 Hz), 3.11 (1H, t, J=6.2 Hz), 3.38-3.48 (1H, m), 3.62-3.98 (6H, m), 4.51-4.68 (2H, m), 6.59 (1H, d, J=9.0 Hz), 7.60 (1H, dd, J=2.2, 9.0 Hz), 8.40 (1H, d, J=2.2 Hz).

EXAMPLE 2

3-((S)-2-amino-2-{cis-4-[4-(5-cyano-2-pyridyl)-1-piperazinyl]-1-cyclohexyl}acetyl)-1,3-thiazolidine

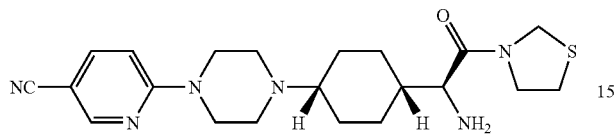

The title compound (83 mg, yield 26%) was obtained as a white powder using the cis form (384 mg) of Example 1 (3) and in the same manner as in Example 1 (4).

¹H-NMR (CDCl₃) δ 1.02-1.37 (4H, m), 1.42-1.75 (2H, m), 1.88-2.02 (3H, m), 2.23-2.36 (1H, m), 2.58-2.68 (4H, m), 3.02 (1H, t, J=6.3 Hz), 3.10 (1H, t, J=6.1 Hz), 3.34 (1H, dd, J=6.1, 10.8 Hz), 3.62-3.98 (6H, m), 4.46-4.70 (2H, m), 6.58 (1H, d, J=8.9 Hz), 7.59 (1H, dd, J=2.3, 8.9 Hz), 8.40 (1H, d, J=2.3 Hz).

EXAMPLE 3

3-((S)-2-amino-2-{trans-4-[4-(3-chloro-5-trifluoromethyl-2-pyridyl)-1-piperazinyl]-1-cyclohexyl}acetyl)-1,3-thiazolidine

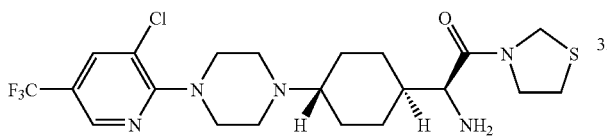

(1) Using the product (514 mg) resulting from Example 1 (2) and 1-(3-chloro-5-trifluoromethyl-2-pyridyl)piperazine (438 mg) and in the same manner as in Example 1 (3), 3-((S)-2-tert-butoxycarbonylamino-2-{4-[4-(3-chloro-5-trifluoromethyl-2-pyridinyl)-1-piperazinyl]-1-cyclohexyl}acetyl)-1,3-thiazolidine was obtained as a white amorphous trans form (490 mg, yield 55.2%) and a white amorphous cis form (254 mg, yield 28.6%).

(2) The title compound (80 mg, yield 20%) was obtained as a white powder using the above-mentioned trans form (484 mg) and in the same manner as in Example 1 (4).

¹H-NMR (DMSO-d₆) δ 1.22-1.86 (9H, m), 2.05-2.27 (2H, brs), 2.57 (4H, s), 2.98 (1H, t, J=6.4 Hz), 3.04-3.13 (1H, m), 3.2-4.0 (8H, m), 4.36-4.82 (2H, m), 8.18 (1H, d, J=2.0 Hz), 8.55 (1H, s).

EXAMPLE 4

3-((S)-2-amino-2-{cis-4-[4-(3-chloro-5-trifluoromethyl-2-pyridyl)-1-piperazinyl]-1-cyclohexyl}acetyl)-1,3-thiazolidine

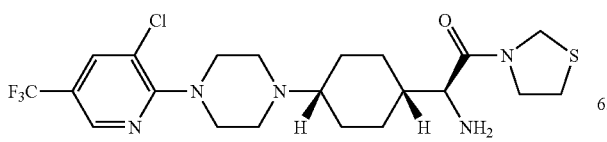

The title compound (25 mg, yield 12%) was obtained as a white powder using the cis form (249 mg) of Example 3 (1) and in the same manner as in Example 1 (4).

¹H-NMR (DMSO-d₆) δ 0.97-1.30 (4H, m), 1.40-1.92 (5H, m), 2.17-2.28 (1H, m), 2.69 (4H, s), 3.01 (1H, t, J=6.4 Hz), 3.07-3.13 (1H, m), 3.20-3.95 (8H, m), 4.37-4.77 (2H, m), 5.06 (brs, 2H), 8.18 (1H, d, J=2.0 Hz), 8.54 (1H, s).

EXAMPLE 5

3-[(S)-2-amino-2-(trans-4-{4-[4-(4-cyanophenyl)-2-thiazolyl]-1-piperazinyl}-1-cyclohexyl)acetyl]-1,3-thiazolidine

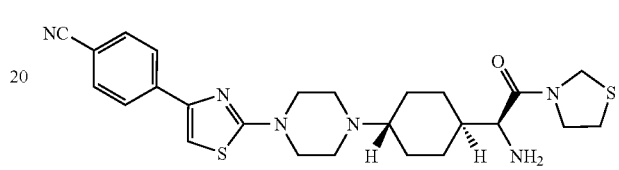

(1) Using the product (342 mg) resulting from Example 1 (2) and 1-[4-(4-cyanophenyl)-2-thiazolyl]piperazine (270 mg) and in the same manner as in Example 1 (3), 3-[(S)-2-tert-butoxycarbonylamino-2-(4-{4-[4-(4-cyanophenyl)-2-thiazolyl]-1-piperazinyl}-1-cyclohexyl)acetyl]-1,3-thiazolidine was obtained as a yellow amorphous trans form (378 mg, yield 63.4%) and a yellow amorphous cis form (195 mg, yield 32.7%).

(2) The title compound (175 mg, yield 55.2%) was obtained as a pale-yellow powder using the above-mentioned trans form (372 mg) and in the same manner as in Example 1 (4).

¹H-NMR (DMSO-d₆) δ 1.25-1.85 (9H, m), 2.17-2.25 (1H, m), 2.52-2.61 (4H, s), 3.00 (1H, t, J=6.4 Hz), 3.04-3.15 (1H, m), 3.25-4.05 (8H, m), 4.18-4.83 (3H, m), 7.59 (1H, s), 7.85 (2H, d, J=8.4 Hz), 8.04 (2H, d, J=8.4 Hz).

EXAMPLE 6

3-[(S)-2-amino-2-(cis-4-{4-[4-(4-cyanophenyl)-2-thiazolyl]-1-piperazinyl}-1-cyclohexyl)acetyl]-1,3-thiazolidine

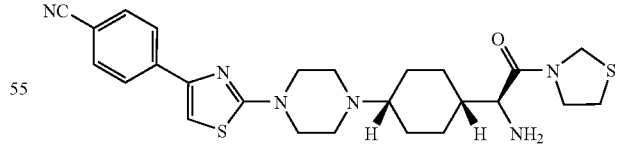

The title compound (43 mg, yield 27%) was obtained as a pale-yellow powder using the cis form (195 mg) of Example 5 (1) and in the same manner as in Example 1 (4).

¹H-NMR (DMSO-d₆) δ 0.97-1.30 (4H, m), 1.40-1.88 (5H, m), 2.18-2.32 (1H, m), 2.55-2.65 (4H, m), 3.01 (1H, t, J=6.4 Hz), 3.06-3.12 (1H, m), 3.25-3.95 (8H, m), 4.30-4.75 (4H, m), 7.58 (1H, s), 7.85 (2H, d, J=8.4 Hz), 8.04 (2H, d, J=8.4 Hz).

EXAMPLE 7

3-((S)-2-amino-2-{trans-4-[4-(3-methyl-1-phenyl-5-pyrazolyl)-1-piperazinyl]-1-cyclohexyl}acetyl)-1,3-thiazolidine trihydrochloride

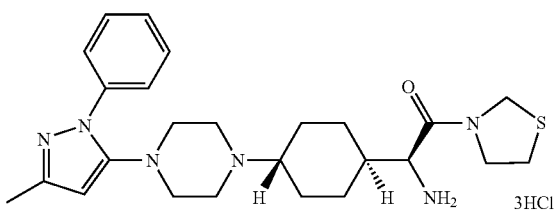

(1) Using the product (514 mg) resulting from Example 1 (2) and 1-(3-methyl-1-phenyl-5-pyrazolyl)piperazine (400 mg) and in the same manner as in Example 1 (3), 3-((S)-2-tert-butoxycarbonylamino-2-{4-[4-(3-methyl-1-phenyl-5-pyrazolyl)-1-piperazinyl]-1-cyclohexyl}acetyl)-1,3-thiazolidine was obtained as a white amorphous trans form (313 mg) and a white amorphous cis form (398 mg).

(2) 3-((S)-2-Amino-2-{trans-4-[4-(3-methyl-1-phenyl-5-pyrazolyl)-1-piperazinyl]-1-cyclohexyl}acetyl)-1,3-thiazolidine (173 mg, yield 68.6%) was obtained as a white amorphous form using the above-mentioned trans form (306 mg) and in the same manner as in Example 1 (4).

(3) The above-mentioned compound (232 mg) was dissolved in ethyl acetate (4 mL), 4 mol/L hydrochloric acid-ethyl acetate (0.40 mL) was added under ice-cooling, and the mixture was stirred for 2 hr. The precipitate was collected by filtration and washed with ethyl acetate to give the title compound (246 mg, yield 85.2%) as a white powder.

$^1$H-NMR (DMSO-$d_6$) δ 1.42-1.58 (2H, m), 1.68-2.10 (7H, m), 2.17 (3H, s), 2.97-4.27 (14H, s), 4.39-4.92 (2H, m), 5.92 (1H, s), 7.32 (1H, t, J=7.5 Hz), 7.48 (2H, t, J=7.5 Hz), 7.77 (1H, d, J=7.5 Hz), 8.41 (1H, brs), 10.63 (1H, brs).

EXAMPLE 8

3-((S)-2-amino-2-{cis-4-[4-(3-methyl-1-phenyl-5-pyrazolyl)-1-piperazinyl]-1-cyclohexyl}acetyl)-1,3-thiazolidine

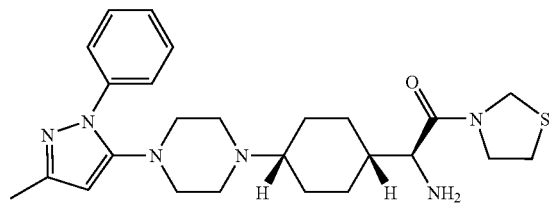

The title compound (60 mg, yield 19%) was obtained as a white powder using a mixture (390 mg) of a trans form and a cis form of Example 7 (1) and in the same manner as in Example 1 (4).

$^1$H-NMR (CDCl$_3$) δ 1.00-1.33 (4H, m), 1.40-1.75 (2H, m), 1.86-2.00 (3H, m), 2.15-2.30 (3H, m), 2.54-2.63 (4H, m), 2.83-2.92 (4H, m), 3.01 (1H, t, J=6.2 Hz), 3.09 (1H, t, J=6.2 Hz), 3.28-3.37 (1H, m), 3.66-3.98 (2H, m), 4.45-4.71 (2H, m), 5.66 (1H, s), 7.23 (1H, t, J=8.0 Hz), 7.40 (1H, t, J=8.0 Hz), 7.76 (1H, d, J=8.0 Hz).

EXAMPLE 9

3-((S)-2-amino-2-{trans-4-[4-(3-bromo-1-isoquinolyl)-1-piperazinyl]-1-cyclohexyl}acetyl)-1,3-thiazolidine trihydrochloride

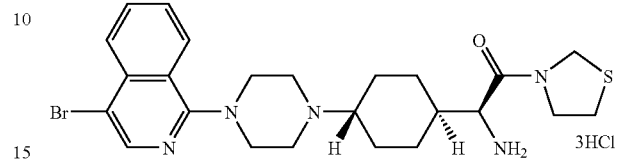

(1) Using the product (514 mg) resulting from Example 1 (2) and 1-(3-bromo-1-isoquinolyl)piperazine (482 mg) and in the same manner as in Example 1 (3), 3-[(S)-2-{4-[4-(3-bromo-1-isoquinolyl)-1-piperazinyl]-1-cyclohexyl}-2-(tert-butoxycarbonylamino)acetyl]-1,3-thiazolidine was obtained as a white amorphous trans form (426 mg) and a white amorphous cis form (375 mg).

(2) 3-((S)-2-Amino-2-{trans-4-[4-(3-bromo-1-isoquinolyl)-1-piperazinyl]-1-cyclohexyl}acetyl)-1,3-thiazolidine (293 mg, yield 84.0%) was obtained as a white amorphous form using the above-mentioned trans form (419 mg) and in the same manner as in Example 1 (4).

(3) The title compound (312 mg, yield 86.9%) was obtained as a white powder using the above-mentioned compound (293 mg) and in the same manner as in Example 7 (3).

$^1$H-NMR (DMSO-$d_6$) δ 1.45-2.20 (9H, m), 3.06 (1H, t, J=6.3 Hz), 3.13 (1H, t, J=6.2 Hz), 3.27-4.33 (12H, m), 4.42-4.94 (2H, m), 7.76 (1H, d, J=7.8 Hz), 7.93 (1H, d, J=7.8 Hz), 8.08 (1H, d, J=7.8 Hz), 8.19 (1H, d, J=7.8 Hz), 8.38 (1H, s), 8.48 (3H, brs), 10.90 (1H, brs).

EXAMPLE 10

3-((S)-2-amino-2-{cis-4-[4-(3-bromo-1-isoquinolyl)-1-piperazinyl]-1-cyclohexyl}acetyl)-1,3-thiazolidine

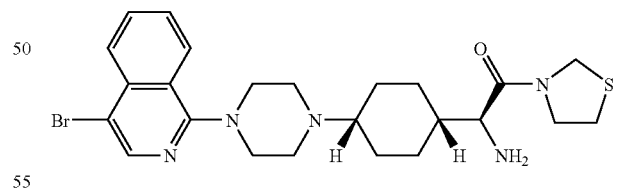

The title compound (70 mg, yield 23%) was obtained as a white powder using a mixture (368 mg) of the trans form and the cis form of Example 9 (1) and in the same manner as in Example 1 (4).

$^1$H-NMR (DMSO-$d_6$) δ 0.90-1.42 (4H, m), 1.52-1.62 (1H, m), 1.73-1.98 (4H, m), 2.18-2.32 (1H, m), 2.69-2.79 (4H, m), 2.99 (1H, t, J=6.4 Hz), 3.08 (1H, t, J=6.3 Hz), 3.26-3.92 (7H, m), 4.36-4.71 (2H, m), 7.71 (1H, d, J=8.0 Hz), 7.85 (1H, d, J=8.0 Hz), 8.02 (1H, d, J=8.0 Hz), 8.12 (1H, d, J=8.0 Hz), 8.32 (1H, s).

EXAMPLE 11

3-((S)-2-amino-2-{trans-4-[4-(2-trifluoromethyl-4-quinolyl)-1-piperazinyl]-1-cyclohexyl}acetyl)-1,3-thiazolidine dihydrochloride

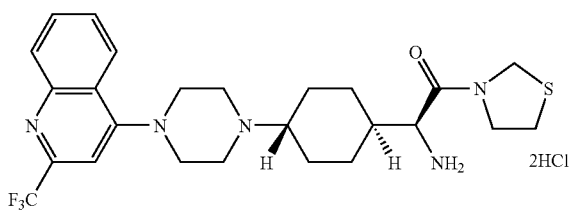

(1) Using the product (514 mg) resulting from Example 1 (2) and 1-(2-trifluoromethyl-4-quinolyl)piperazine (464 mg) and in the same manner as in Example 1 (3), 3-((S)-2-tert-butoxycarbonylamino-2-{4-[4-(2-trifluoromethyl-4-quinolyl)-1-piperazinyl]-1-cyclohexyl}acetyl)-1,3-thiazolidine was obtained as a pale-yellow amorphous trans form (578 mg, yield 63.4%), and a colorless cis oil (127 mg, yield 13.9%).
(2) 3-((S)-2-Amino-2-{trans-4-[4-(2-trifluoromethyl-4-quinolyl)-1-piperazinyl]-1-cyclohexyl}acetyl)-1,3-thiazolidine (325 mg, yield 68.0%) was obtained as a yellow oil using the above-mentioned trans form (572 mg) and in the same manner as in Example 1 (4).
(3) The title compound (381 mg, yield 96.6%) was obtained as a white powder using the above-mentioned compound (325 mg) and in the same manner as in Example 7 (3).
$^1$H-NMR (DMSO-$d_6$) δ 1.45-1.63 (2H, m), 1.75-2.22 (7H, m), 3.06 (1H, t, J=6.3 Hz), 3.14 (1H, t, J=6.1 Hz), 3.31-3.53 (3H, m), 3.60-4.95 (11H, m), 7.37 (1H, s), 7.48 (1H, t, J=7.2 Hz), 7.89 (1H, t, J=7.2 Hz), 8.05-8.18 (2H, m), 8.50 (3H, brs).

EXAMPLE 12

3-((S)-2-amino-2-{cis-4-[4-(2-trifluoromethyl-4-quinolyl)-1-piperazinyl]-1-cyclohexyl}acetyl)-1,3-thiazolidine dihydrochloride

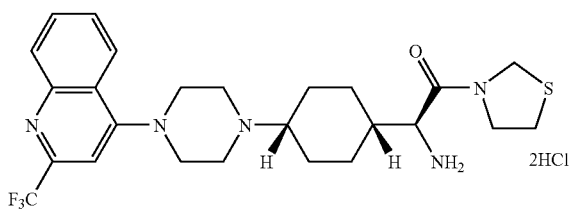

(1) 3-((S)-2-Amino-2-{cis-4-[4-(2-trifluoromethyl-4-quinolyl)-1-piperazinyl]-1-cyclohexyl}acetyl)-1,3-thiazolidine (81 mg, yield 76%) was obtained as a colorless oil using the cis form (127 mg) of Example 11 (1) and in the same manner as in Example 1 (4).
(2) The title compound (82 mg, yield 83%) was obtained as a white powder using the above-mentioned compound (81 mg) and in the same manner as in Example 7 (3).
$^1$H-NMR (DMSO-$d_6$) δ 1.13-1.98 (7H, m), 2.23-2.38 (2H, m), 3.02-3.29 (3H, m), 3.38-4.23 (11H, m), 4.39-4.87 (2H, m), 7.36 (1H, s), 7.74 (1H, t, J=7.8 Hz), 7.89 (1H, t, J=7.8 Hz), 8.13 (1H, d, J=7.8 Hz), 8.17 (1H, d, J=7.8 Hz), 8.42 (3H, brs).

EXAMPLE 13

3-((S)-2-amino-2-{trans-4-[4-(2-benzothiazolyl)-1-piperazinyl]-1-cyclohexyl}acetyl)-1,3-thiazolidine

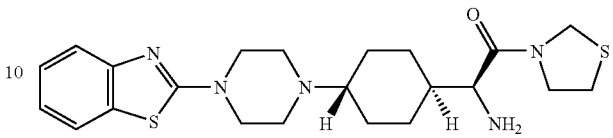

(1) Using the product (514 mg) resulting from Example 1 (2) and 1-(2-benzothiazolyl)piperazine (362 mg) and in the same manner as in Example 1 (3), 3-[(S)-2-{4-[4-(2-benzothiazolyl)-1-piperazinyl]-1-cyclohexyl}-2-(tert-butoxycarbonylamino)acetyl]-1,3-thiazolidine as a trans form (488 mg, yield 59.6%), and a white cis solid (279 mg, yield 34.1%).
(2) The title compound (247 mg, yield 62.9%) was obtained as a white powder using the above-mentioned trans form (481 mg) and in the same manner as in Example 1 (4).
$^1$H-NMR (DMSO-$d_6$) δ 1.20-1.83 (9H, m), 2.20 (1H, brs), 2.52-2.67 (4H, m), 2.98 (1H, t, J=6.4 Hz), 3.09 (1H, t, J=6.4 Hz), 3.24-4.00 (9H, m), 4.36-4.82 (2H, m), 7.07 (1H, t, J=7.7 Hz), 7.27 (1H, t, J=7.7 Hz), 7.45 (1H, d, J=7.7 Hz), 7.76 (1H, d, J=7.7 Hz).

EXAMPLE 14

3-((S)-2-amino-2-{cis-4-[4-(2-benzothiazolyl)-1-piperazinyl]-1-cyclohexyl}acetyl)-1,3-thiazolidine

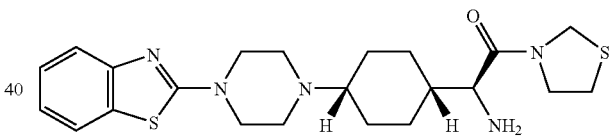

The title compound (98 mg, yield 44%) was obtained as a white powder using the cis form (273 mg) of Example 13 (1) and in the same manner as in Example 1 (4).
$^1$H-NMR (DMSO-$d_6$) δ 0.88-1.98 (9H, m), 2.17-2.33 (1H, m), 2.53-2.68 (4H, m), 2.98 (1H, t, J=6.5 Hz), 3.07 (1H, t, J=6.2 Hz), 3.20-3.92 (9H, m), 4.35-4.71 (2H, m), 7.06 (1H, t, J=8.0 Hz), 7.27 (1H, t, J=8.0 Hz), 7.44 (1H, d, J=8.0 Hz), 7.75 (1H, d, J=8.0 Hz).

EXAMPLE 15

3-((S)-2-amino-2-{4-[4-(2-benzimidazolyl)piperidino]-1-cyclohexyl}acetyl)-1,3-thiazolidine trihydrochloride

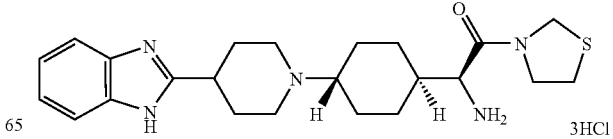

(1) The product (688 mg) resulting from Example 1 (2), 1-(2-benzimidazolyl)piperidine (445 mg) and acetic acid (0.12 mL) were dissolved in methanol (12 mL), sodium cyanoborohydride (140 mg) was added, and the mixture was stirred at room temperature for 28 hr. The reaction mixture was concentrated, and saturated aqueous sodium hydrogencarbonate solution was added to the residue. The mixture was extracted with chloroform and the extract was washed with saturated brine and dried. The solvent was evaporated under reduced pressure and the residue was purified by silica gel chromatography to give 3-[(S)-2-{4-[4-(2-benzimidazolyl)piperidino]-1-cyclohexyl}-2-(tert-butoxycarbonylamino)acetyl]-1,3-thiazolidine (445 mg, yield 42.0%) as a pale-yellow amorphous form.

(2) The above-mentioned compound (404 mg) was dissolved in ethanol (3 mL), 4 mol/L hydrochloric acid-1,4-dioxane (3 mL) was added, and the mixture was stirred for 6 hr. The reaction mixture was concentrated under reduced pressure and ethyl acetate (10 mL) was added to the residue. The solid was collected by filtration and washed with ethyl acetate to give the title compound (322 mg, yield 78.3%) as a white powder.

$^1$H-NMR (DMSO-$d_6$) δ 1.15-2.13 (8H, m), 2.18-2.32 (1H, m), 3.0-5.0 (17H, m), 7.49-7.59 (2H, m), 7.75-7.86 (2H, m), 8.40, 8.48 (3H, brs), 10.7, 11.1 (1H, brs).

EXAMPLE 16

3-{(S)-2-amino-2-[trans-4-(4-phenyl-1-piperazinyl)-1-cyclohexyl]acetyl}-1,3-thiazolidine

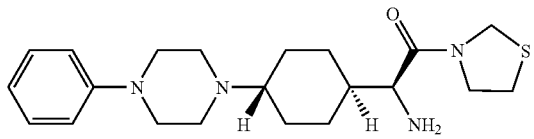

(1) Using the product (630 mg) resulting from Example 1 (2) and 1-phenylpiperazine (381 mg) and in the same manner as in Example 1 (3), 3-{(S)-2-tert-butoxycarbonylamino-3-[trans-4-(4-phenyl-1-piperazinyl)-1-cyclohexyl]acetyl}-1,3-thiazolidine was obtained as a white amorphous trans form (495 mg), and a mixture (409 mg) of the trans form and a cis form in a white amorphous form.

(2) The title compound (156 mg, yield 39.0%) was obtained as a white needle crystal using the above-mentioned trans form (487 mg) and in the same manner as in Example 1 (4).

$^1$H-NMR (CDCl$_3$) δ 1.35-1.97 (9H, m), 2.18-2.27 (1H, m), 2.58-2.70 (4H, m), 3.01 (1H, t, J=6.5 Hz), 3.10 (1H, t, J=6.2 Hz), 3.16-3.26 (4H, m), 3.39-3.51 (1H, m), 3.72-3.98 (2H, m), 4.52-4.70 (2H, m), 6.85 (1H, t, J=7.8 Hz), 6.93 (2H, d, J=7.8 Hz), 7.26 (2H, t, J=7.8 Hz).

EXAMPLE 17

3-{(S)-2-amino-2-[cis-4-(4-phenyl-1-piperazinyl)-1-cyclohexyl]acetyl}-1,3-thiazolidine

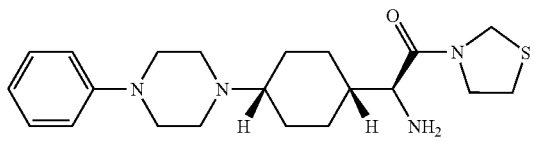

The title compound (25 mg, yield 9.5%) was obtained as a white powder using a mixture (403 mg) of the trans form and the cis form of Example 16 (1) and in the same manner as in Example 1 (4).

$^1$H-NMR (CDCl$_3$) δ 1.04-1.78 (6H, m), 1.92-2.10 (3H, m), 2.23-2.37 (1H, m), 2.70-2.78 (4H, m), 3.01 (1H, t, J=6.4 Hz), 3.10 (1H, t, J=6.2 Hz), 3.17-3.26 (4H, m), 3.31-3.39 (1H, m), 3.78-3.98 (2H, m), 4.47-4.71 (2H, m), 6.85 (1H, t, J=7.8 Hz), 6.93 (2H, d, J=7.8 Hz), 7.26 (2H, t, J=7.8 Hz).

EXAMPLE 18

3-{(S)-2-amino-3-[trans-4-(4-phenyl-1-piperazinyl)-1-cyclohexyl]propionyl}-1,3-thiazolidine

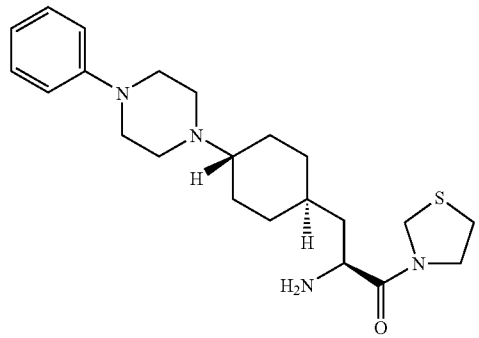

(1) 3-[(S)-2-tert-Butoxycarbonylamino-3-(4-hydroxy-1-cyclohexyl)propionyl]-1,3-thiazolidine (44.6 g, yield 88.9%) was obtained as a white amorphous form using L-tyrosine (25.4 g) and in the same manner as in Example 1 (1).

(2) 3-[(S)-2-tert-Butoxycarbonylamino-3-(4-oxo-1-cyclohexyl)propionyl]-1,3-thiazolidine (30.0 g, yield 71.9%) was obtained as a colorless highly viscose oil using the above-mentioned compound (42.0 g) and in the same manner as in Example 1 (2).

$^1$H-NMR (CDCl$_3$) δ 1.43 (9H, s), 1.32-1.70 (4H, m), 1.82-2.08 (2H, m), 2.28-2.45 (5H, m), 3.02 (1H, t, J=6.3 Hz), 3.08-3.17 (1H, m), 4.43-4.73 (3H, m), 5.29 (1H, d, J=8.9 Hz).

(3) Using the above-mentioned compound (740 mg) and 1-phenylpiperazine (0.35 mL) and in the same manner as in Example 1 (3), 3-[(S)-2-tert-butoxycarbonylamino-3-(4-oxo-1-cyclohexyl)propionyl]-1,3-thiazolidine was obtained as a white amorphous trans form (496 mg) and a mixture (379 mg) of the trans form and a cis form in a white amorphous form.

(4) The title compound (216 mg, yield 54.4%) was obtained as a pale-yellow powder using the above-mentioned trans form (487 mg) and in the same manner as in Example 1 (4).

$^1$H-NMR (CDCl$_3$) δ 1.32-1.44 (1H, m), 1.48-1.92 (10H, m), 2.21-2.29 (1H, m), 2.64-2.73 (4H, m), 3.01 (1H, t, J=6.3 Hz), 3.11 (1H, t, J=6.1 Hz), 3.15-3.26 (4H, m), 3.52-3.96 (3H, m), 4.43-4.68 (2H, m), 6.85 (1H, t, J=7.5 Hz), 6.93 (2H, d, J=7.5 Hz), 7.26 (2H, t, J=7.5 Hz).

EXAMPLE 19

3-{(S)-2-amino-3-[cis-4-(4-phenyl-1-piperazinyl)-1-cyclohexyl]propionyl}-1,3-thiazolidine trihydrochloride

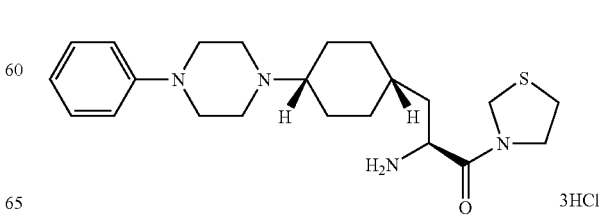

(1) 3-{(S)-2-Amino-3-[cis-4-(4-phenyl-1-piperazinyl)-1-cyclohexyl]propionyl}-1,3-thiazolidine (252 mg, yield 86.0%) was obtained as a yellow oil using a mixture (379 mg) of the trans form and the cis form of Example 18 (3) and in the same manner as in Example 1 (4).

(2) The title compound (166 mg, yield 83.7%) was obtained as a white powder using the above-mentioned compound (150 mg) and in the same manner as in Example 7 (3).

$^1$H-NMR (DMSO-d$_6$) δ 0.88-1.14 (1H, m), 1.43-2.28 (10H, m), 3.02-4.08 (13H, m), 4.20-4.94 (3H, m), 6.87 (1H, t, J=7.5 Hz), 7.00 (2H, d, J=7.5 Hz), 7.27 (2H, t, J=7.5 Hz), 8.33 (3H, brs), 11.0 (1H, brs).

EXAMPLE 20

3-((S)-2-amino-3-{trans-4-[4-(5-cyano-2-pyridyl)-1-piperazinyl]-1-cyclohexyl}propionyl)-1,3-thiazolidine

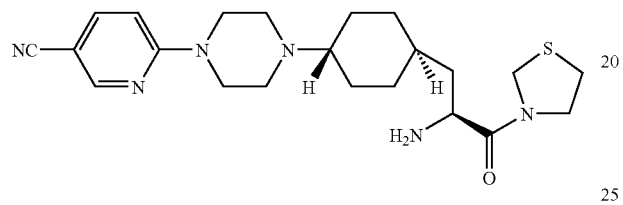

(1) Using the product (798 mg) resulting from Example 18 (2) and 1-(5-cyano-2-pyridyl)piperazine (463 mg) and in the same manner as in Example 1 (3), 3-((S)-2-tert-butoxycarbonylamino-3-{trans-4-[4-(5-cyano-2-pyridyl)-1-piperazinyl]-1-cyclohexyl}propionyl)-1,3-thiazolidine was obtained as a white amorphous trans form (607 mg, yield 51.3%) and a brown cis oil (393 mg, yield 33.2%).

(2) The title compound (201 mg, yield 41.3%) was obtained as a white powder using the above-mentioned trans form (598 mg) and in the same manner as in Example 1 (4).

$^1$H-NMR (CDCl$_3$) δ 1.32-1.92 (11H, m), 2.20-2.29 (1H, m), 2.53-2.66 (4H, m), 3.01 (1H, t, J=6.3 Hz), 3.12 (1H, t, J=6.2 Hz), 3.51-3.96 (7H, m), 4.43-4.68 (2H, m), 6.59 (1H, d, J=9.1 Hz), 7.60 (1H, dd, J=2.3, 9.1 Hz), 8.40 (1H, d, J=2.3 Hz).

EXAMPLE 21

3-((S)-2-amino-3-{cis-4-[4-(5-cyano-2-pyridyl)-1-piperazinyl]-1-cyclohexyl}propionyl)-1,3-thiazolidine

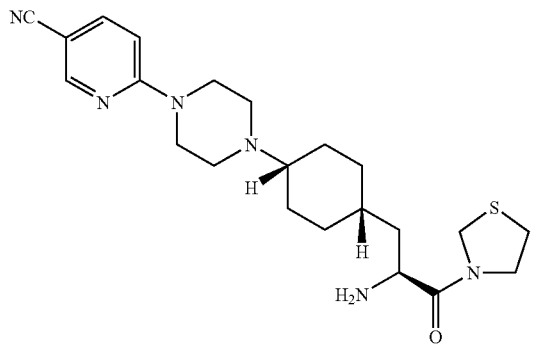

The title compound (42 mg, yield 13%) was obtained as a white powder using the cis form (393 mg) of Example 20 (1) and in the same manner as in Example 1 (4).

$^1$H-NMR (CDCl$_3$) δ 0.87-1.12 (2H, m), 1.23-2.04 (9H, m), 2.26-2.35 (1H, m), 2.63-2.69 (4H, m), 3.01 (1H, t, J=6.4 Hz), 3.10 (1H, t, J=6.1 Hz), 3.53-3.94 (7H, m), 4.38-4.67 (2H, m), 6.58 (1H, d, J=9.1 Hz), 7.59 (1H, dd, J=2.4, 9.1 Hz), 8.40 (1H, d, J=2.4 Hz).

EXAMPLE 22

3-((S)-2-amino-3-{trans-4-[4-(3-methyl-1-phenyl-5-pyrazolyl)-1-piperazinyl]-1-cyclohexyl}propionyl)-1,3-thiazolidine trihydrochloride

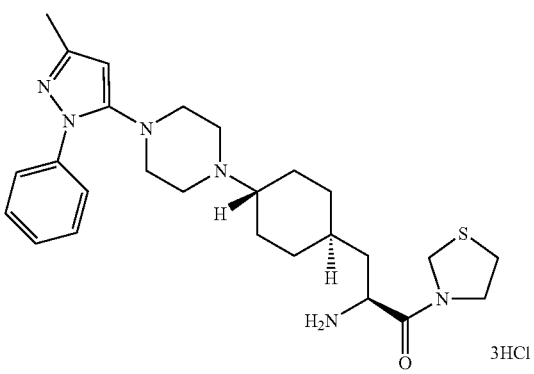

(1) Using the product (702 mg) resulting from Example 18 (2) and 1-(3-methyl-1-phenyl-5-pyrazolyl)piperazine (525 mg) and in the same manner as in Example 1 (3), 3-((S)-2-tert-butoxycarbonylamino-3-{4-[4-(3-methyl-1-phenyl-5-pyrazolyl)-1-piperazinyl]-1-cyclohexyl}propionyl)-1,3-thiazolidine was obtained as a white amorphous trans form (477 mg) and a mixture (431 mg) of the trans form and a cis form in a white amorphous form.

(2) 3-((S)-2-Amino-3-{trans-4-[4-(3-methyl-1-phenyl-5-pyrazolyl)-1-piperazinyl]-1-cyclohexyl}propionyl)-1,3-thiazolidine (286 mg, yield 73.5%) was obtained as a yellow oil using the above-mentioned trans form (470 mg) and in the same manner as in Example 1 (4).

(3) The title compound (257 mg, yield 71.0%) was obtained as a white powder using the above-mentioned compound (286 mg) and in the same manner as in Example 7 (3).

$^1$H-NMR (DMSO-d$_6$) δ 1.38-1.97 (11H, m), 2.17 (3H, s), 2.95-3.32 (9H, m), 3.42-3.53 (2H, m), 3.68-3.98 (2H, m), 4.13-4.90 (3H, m), 5.91 (1H, s), 7.31 (1H, t, J=7.5 Hz), 7.47 (2H, t, J=7.5 Hz), 7.79 (2H, d, J=7.5 Hz), 8.34 (3H, brs), 11.2 (1H, brs).

EXAMPLE 23

3-((S)-2-amino-3-{cis-4-[4-(3-methyl-1-phenyl-5-pyrazolyl)-1-piperazinyl]-1-cyclohexyl}propionyl)-1,3-thiazolidine trihydrochloride

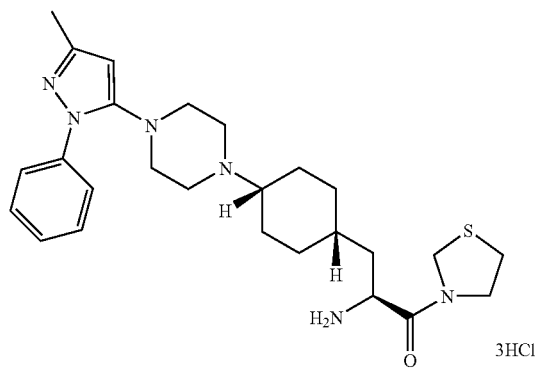

(1) 3-((S)-2-Amino-3-{cis-4-[4-(3-methyl-1-phenyl-5-pyrazolyl)-1-piperazinyl]-1-cyclohexyl}propionyl)-1,3-thiazolidine (135 mg, yield 38.2%) was obtained as a colorless oil using a mixture (427 mg) of the trans form and the cis form of Example 22 (1) and in the same manner as in Example 1 (4).

(2) The title compound (122 mg, yield 72.1%) was obtained as a white powder using the above-mentioned compound (135 mg) and in the same manner as in Example 7 (3).

$^1$H-NMR (DMSO-$d_6$) δ 0.85-1.10 (2H, m), 1.38-2.24 (13H, m), 2.97-3.28 (9H, m), 3.42-4.03 (3H, m), 4.15-4.88 (3H, m), 5.91 (1H, s), 7.31 (1H, t, J=7.8 Hz), 7.48 (2H, t, J=7.8 Hz), 7.77 (2H, d, J=7.8 Hz), 8.35 (3H, brs), 11.3 (1H, brs).

EXAMPLE 24

3-{(S)-2-amino-3-[trans-4-(4-nitrobenzylamino)-1-cyclohexyl]propionyl}-1,3-thiazolidine dihydrochloride

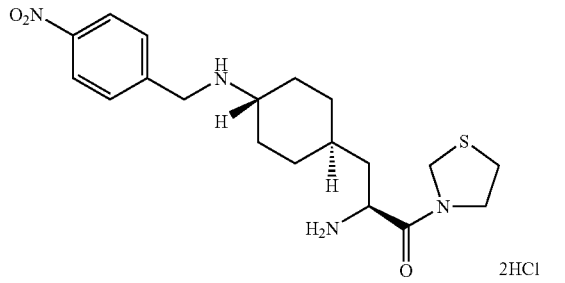

(1) The product (535 mg) resulting from Example 18 (2), triethylamine (0.28 mL) and 4-nitrobenzylamine hydrochloride (311 mg) were dissolved in chloroform (7 mL), sodium triacetoxyborohydride (636 mg) was added, and the mixture was stirred at room temperature for 5 hr. Saturated aqueous sodium hydrogencarbonate solution was added to the reaction mixture, and the mixture was extracted with chloroform. The extract was washed with saturated brine and dried. The solvent was evaporated under reduced pressure and the residue was purified by silica gel chromatography to give 3-{(S)-2-tert-butoxycarbonylamino-3-[4-(4-nitrobenzylamino)-1-cyclohexyl]propionyl}-1,3-thiazolidine was obtained as a white amorphous trans form (412 mg) and a mixture (345 mg) of the trans form and a cis form in a white amorphous form.

(2) 3-{(S)-2-Amino-3-[trans-4-(4-nitrobenzylamino)-1-cyclohexyl]propionyl}-1,3-thiazolidine (312 mg, yield 96.0%) was obtained as a yellow oil using the above-mentioned trans form (408 mg) and in the same manner as in Example 1 (4).

(3) The title compound (314 mg, yield 81.7%) was obtained as a white powder using the above-mentioned compound (312 mg) and in the same manner as in Example 7 (3).

$^1$H-NMR (CDCl$_3$) δ 1.42-1.93 (11H, m), 3.02-4.05 (6H, m), 4.12-4.93 (4H, m), 7.94 (2H, d, J=8.6 Hz), 8.28 (2H, d, J=8.6 Hz), 8.40 (brs, 2H).

EXAMPLE 25

3-{(S)-2-amino-3-[cis-4-(4-nitrobenzylamino)-1-cyclohexyl]propionyl}-1,3-thiazolidine dihydrochloride

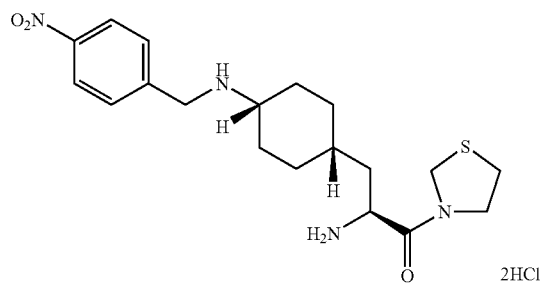

(1) 3-{(S)-2-Amino-3-[cis-4-(4-nitrobenzylamino)-1-cyclohexyl]propionyl}-1,3-thiazolidine (115 mg, yield 42.7%) was obtained as a colorless oil using a mixture (338 mg) of the trans form and the cis form of Example 24 (1) and in the same manner as in Example 1 (4).

(2) The title compound (132 mg, yield 93.2%) was obtained as a white powder using the above-mentioned compound (115 mg) and in the same manner as in Example 7 (3).

$^1$H-NMR (DMSO-$d_6$) δ 0.82-1.08 (2H, m), 1.37-1.72 (6H, m), 1.90-2.19 (3H, m), 2.77-3.96 (5H, m), 4.15-4.83 (5H, m), 7.89 (2H, d, J=8.6 Hz), 8.28 (2H, d, J=8.6 Hz), 8.55 (brs, 2H).

EXAMPLE 26

3-[(S)-2-amino-3-(4-anilino-1-cyclohexyl)propionyl]-1,3-thiazolidine dihydrochloride

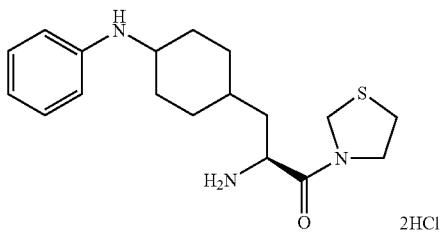

(1) 3-[(S)-3-(4-Anilino-1-cyclohexyl)-2-tert-(butoxycarbonylamino)propionyl]-1,3-thiazolidine (584 mg, yield 67.3%) was obtained as a white amorphous form using the product (713 mg) resulting from Example 18 (2) and aniline (0.20 mL) and in the same manner as in Example 1 (3).

(2) 3-[(S)-2-Amino-3-(4-anilino-1-cyclohexyl)propionyl]-1,3-thiazolidine (391 mg, yield 93.8%) was obtained as a colorless oil using the above-mentioned compound (542 mg) and in the same manner as in Example 1 (4).

(3) The title compound (427 mg, yield 88.6%) was obtained as a white powder using the above-mentioned compound (391 mg) and in the same manner as in Example 7 (3).

$^1$H-NMR (DMSO-$d_6$) δ 0.88-1.11 (1H, m), 1.34-2.00 (10H, m), 2.98-4.08 (4H, m), 4.15-4.93 (4H, m), 7.00-7.48 (5H, m), 8.30 (brs, 3H).

The compound of the present invention showed a potent DPP-IV inhibitory activity in Experimental Example 1 shown below.

EXPERIMENTAL EXAMPLE 1

(Plasma DPP-IV Inhibitory Activity)

The plasma DPP-IV inhibitory activity of human and rat was measured by the fluorescence assay method. Using Gly-Pro-MCA (Peptide Institute Inc.) as a DPP-IV specific fluorescent substrate, reaction solutions having the following compositions and containing test substances having various concentrations were incubated at room temperature for 60 min and the measured (SPECTRA FLUOR, TECAN) fluorescent intensity (Excitation 360 nm/Emission 465 nm) was taken as the DPP-IV activity.

As a buffer, 0.003% Brij-35-containing phosphate buffer (PBS, Sigma-Aldrich Co.) was used.

A reaction solution free of the test substance was used as a control.

TABLE 1

| | |
|---|---|
| Rat or human plasma (10-fold diluted solution) | 20 µL/well |
| fluorescent substrate (100 µmol/L) | 20 µL/well |
| test substance | 20 µL/well |
| buffer | 140 µL/well |
| total amount | 200 µL/well |

The inhibitory rate of the test substance relative to the reaction of the control was calculated, and $IC_{50}$ values were determined by logistic analysis. The $IC_{50}$ values of the plasma DPP-IV inhibitory activity of the present invention as determined by the above method are shown in the following table.

TABLE 2

| Example compound No. | Human plasma DPP-IV inhibitory activity $IC_{50}$ (nM) | Rat plasma DPP-IV inhibitory activity $IC_{50}$ (nM) |
|---|---|---|
| 2 | 1.6 | 1.4 |
| 14 | 2.1 | 1.4 |

INDUSTRIAL APPLICABILITY

From the foregoing Experimental Examples, the α-amino acid derivative of the present invention exhibits a potent DPP-IV inhibitory activity and is useful for the prophylaxis and/or treatment of diabetes, or the prophylaxis and/or treatment of obesity.

This application is based on a patent application No. 2003-413846 filed in Japan, the contents of which are incorporated in full herein by this reference.

The invention claimed is:

1. An α-amino acid derivative of the formula (I)

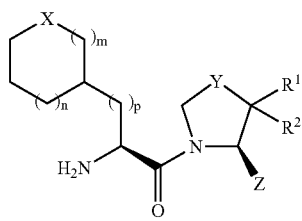

(I)

wherein
  $R^1$ is a hydrogen atom, a halogen atom, alkyl or alkoxy,
  $R^2$ is a hydrogen atom, a halogen atom, a hydroxyl group, alkyl or alkoxy, or
  $R^1$ and $R^2$ are joined to form oxo, hydroxyimino, alkoxyimino or alkylidene,
  X is CH—$R^3$,
  Y is S,
  Z is a hydrogen atom or cyano,
  m and n are each 0, 1 or 2, wherein the sum of m and n is 2,
  when p is 1,
  $R^3$ is —$NR^7R^8$
    wherein $R^7$ and $R^8$ are optionally the same or different and each independently is a hydrogen atom, alkyl, cycloalkyl, cycloalkylalkyl, aryl, arylalkyl, heteroaryl or heteroarylalkyl, or are optionally bonded to each other to form heterocycle having at least one nitrogen atom, and optionally having other further hetero atom(s),
      wherein the heterocycle is optionally substituted or condensed with an aromatic ring optionally having substituent(s),
  —$NR^9COR^{10}$
    wherein $R^9$ and $R^{10}$ are optionally the same or different and each independently is a hydrogen atom, alkyl, cycloalkyl, cycloalkylalkyl, aryl, arylalkyl, arylalkenyl, heteroaryl, heteroarylalkyl or heterocycle,
  —$NR^{11}CONR^{12}R^{13}$
    wherein $R^{11}$, $R^{12}$ and $R^{13}$ are optionally the same or different and each independently is a hydrogen atom, alkyl, cycloalkyl, cycloalkylalkyl, aryl, arylalkyl, heteroaryl or heteroarylalkyl, or $R^{12}$ and $R^{13}$ are optionally bonded to each other to form heterocycle having at least one nitrogen atom, and optionally having other further hetero atom(s),
      wherein the heterocycle is optionally substituted or condensed with an aromatic ring optionally having substituent(s),
  —$NR^{14}SO_2R^{15}$
    wherein $R^{14}$ and $R^{15}$ are optionally the same or different and each independently is a hydrogen atom, alkyl, cycloalkyl, cycloalkylalkyl, aryl, arylalkyl, heteroaryl, heteroarylalkyl or heterocycle,
  —$OR^{16}$ or —$OCOR^{17}$
    wherein $R^{16}$ and $R^{17}$ are each a hydrogen atom, alkyl, cycloalkyl, cycloalkylalkyl, aryl, arylalkyl, heteroaryl, heteroarylalkyl or heterocycle, and
  when p is 0, and $R^3$ is of formula (II)

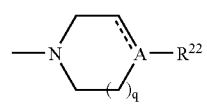

(II)

wherein
  ----- is a single bond or a double bond,
  $R^{22}$ is aryl or heteroaryl,
  Q is 1 or 2, and
  A is a carbon atom or a nitrogen atom,
    provided that i) when A is a carbon atom, then A is optionally substituted by a hydroxyl group, carboxyl or alkoxycarbonyl, and ii) when A is a nitrogen atom, then
      ----- is a single bond, wherein, of the above-mentioned groups, alkyl, cycloalkyl, cycloalkylalkyl, aryl, arylalkyl, heteroaryl, heteroarylalkyl and heterocycle optionally have substituent(s), or a pharmaceutically acceptable salt thereof.

2. The α-amino acid derivative of claim 1, wherein m=2 and n=0.

3. The α-amino acid derivative of claim 1, wherein $R^3$ is the formula (II).

4. The α-amino acid derivative of claim 3, wherein $R^1=R^2=Z=H$, q=1 and A=N.

5. A pharmaceutical composition comprising an α-amino acid derivative of claim 1 or a pharmaceutically acceptable salt thereof and a pharmacologically acceptable carrier.

6. A method of producing a compound of claim 1, which comprises a method of producing a compound of formula (III)

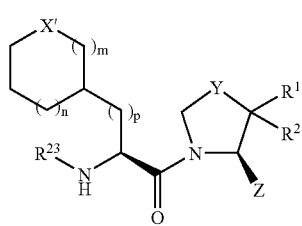

wherein
X' is CH—$R^3$,
$R^{23}$ is —$COR^{24}$
    wherein $R^{24}$ is a hydrogen atom, alkyl, cycloalkyl, cycloalkylalkyl, aryl, arylalkyl, heteroaryl, heteroarylalkyl or heterocycle, or
—$COOR^{25}$
    wherein $R^{25}$ is alkyl, cycloalkyl, cycloalkylalkyl, aryl, arylalkyl, heteroaryl, heteroarylalkyl or heterocycle,
$R^1$ is a hydrogen atom, a halogen atom, alkyl or alkoxy,
$R^2$ is a hydrogen atom, a halogen atom, a hydroxyl group, alkyl or alkoxy, or
$R^1$ and $R^2$ are joined to form oxo, hydroxyimino, alkoxyimino or alkylidene,
Y is S,
Z is a hydrogen atom or cyano,
m and n are each 0, 1 or 2, wherein the sum of m and n is 2,
p is 0 or 1
$R^3$ is —$NR^7R^8$
    wherein $R^7$ and $R^8$ are optionally the same or different and each independently is a hydrogen atom, alkyl, cycloalkyl, cycloalkylalkyl, aryl, arylalkyl, heteroaryl or heteroarylalkyl, or are optionally bonded to each other to form heterocycle having at least one nitrogen atom, and optionally having other further hetero atom(s),
        wherein the heterocycle is optionally substituted or condensed with an aromatic ring optionally having substituent(s),
—$NR^9COR^{10}$
    wherein $R^9$ and $R^{10}$ are optionally the same or different and each independently is a hydrogen atom, alkyl, cycloalkyl, cycloalkylalkyl, aryl, arylalkyl, arylalkenyl, heteroaryl, heteroarylalkyl or heterocycle,
—$NR^{11}CONR^{12}R^{13}$
    wherein $R^{11}$, $R^{12}$ and $R^{13}$ are optionally the same or different and each independently is a hydrogen atom, alkyl, cycloalkyl, cycloalkylalkyl, aryl, arylalkyl, heteroaryl or heteroarylalkyl, or $R^{12}$ and $R^{13}$ are optionally bonded to each other to form heterocycle having at least one nitrogen atom, and optionally having other further hetero atom(s),
        wherein the heterocycle is optionally substituted or condensed with an aromatic ring optionally having substituent(s),
—$NR^{14}SO_2R^{15}$
    wherein $R^{14}$ and $R^{15}$ are optionally the same or different and each independently is a hydrogen atom, alkyl, cycloalkyl, cycloalkylalkyl, aryl, arylalkyl, heteroaryl, heteroarylalkyl or heterocycle,
—$OR^{16}$ or —$OCOR^{17}$
    wherein $R^{16}$ and $R^{17}$ are each a hydrogen atom, alkyl, cycloalkyl, cycloalkylalkyl, aryl, arylalkyl, heteroaryl, heteroarylalkyl or heterocycle, and
wherein, of the above-mentioned groups, alkyl, cycloalkyl, cycloalkylalkyl, aryl, arylalkyl, heteroaryl, heteroarylalkyl and heterocycle optionally have substituent(s)
comprising use of a compound of formula (III) in which X' is C=O as an intermediate.

7. A method of therapeutically treating type II diabetes or obesity in a subject comprising administering to a subject in need thereof an effective amount of a compound of claim 1 to treat type II diabetes or obesity in the subject.

8. A method of therapeutically treating type II diabetes or obesity in a subject comprising administering to a subject in need thereof an effective amount of a compound of claim 2 to treat type II diabetes or obesity in the subject.

9. A method of therapeutically treating type II diabetes or obesity in a subject comprising administering to a subject in need thereof an effective amount of a compound of claim 3 to treat type II diabetes or obesity in the subject.

10. A method of therapeutically treating type II diabetes or obesity in a subject comprising administering to a subject in need thereof an effective amount of a compound of claim 4 to treat type II diabetes or obesity in the subject.

* * * * *

UNITED STATES PATENT AND TRADEMARK OFFICE
CERTIFICATE OF CORRECTION

PATENT NO. : 7,504,423 B2
APPLICATION NO. : 10/582602
DATED : March 17, 2009
INVENTOR(S) : Akahoshi et al.

It is certified that error appears in the above-identified patent and that said Letters Patent is hereby corrected as shown below:

TITLE PAGE OF THE PATENT ITEM (56),

Under heading "OTHER PUBLICATIONS"

Wiedeman et al., *Current Opinion in Investigation Drugs*, 4(4): 412-420 (2003).

should read

Wiedeman et al., *Current Opinion in Investigational Drugs*, 4(4): 412-420 (2003).

Signed and Sealed this

Eighth Day of September, 2009

David J. Kappos
*Director of the United States Patent and Trademark Office*